US008623830B2

(12) United States Patent
Flier et al.

(10) Patent No.: US 8,623,830 B2
(45) Date of Patent: Jan. 7, 2014

(54) COMPOSITIONS CONTAINING α-1-ANTITRYPSIN AND METHODS FOR USE

(75) Inventors: Jeffrey Flier, Newton, MA (US); Maria Koulmanda, Brookline, MA (US); Terry B. Strom, Brookline, MA (US)

(73) Assignees: Beth Israel Deaconess Medical Center, Inc., Boston, MA (US); The General Hospital Corporation, Boston, MA (US)

( * ) Notice: Subject to any disclaimer, the term of this patent is extended or adjusted under 35 U.S.C. 154(b) by 766 days.

(21) Appl. No.: 12/441,064

(22) PCT Filed: Sep. 12, 2007

(86) PCT No.: PCT/US2007/078231
§ 371 (c)(1),
(2), (4) Date: Jan. 4, 2010

(87) PCT Pub. No.: WO2008/033890
PCT Pub. Date: Sep. 12, 2007

(65) Prior Publication Data
US 2010/0111940 A1 May 6, 2010

Related U.S. Application Data

(60) Provisional application No. 60/844,003, filed on Sep. 12, 2006.

(51) Int. Cl.
*A61K 38/48* (2006.01)
*A61K 38/55* (2006.01)
*C07K 14/81* (2006.01)
*A61K 39/00* (2006.01)
*A61K 39/395* (2006.01)
*C07K 1/00* (2006.01)
*C07K 14/00* (2006.01)
*C07K 17/00* (2006.01)

(52) U.S. Cl.
USPC ............ 514/20.1; 424/133.1; 424/153.1; 424/173.1; 530/350

(58) Field of Classification Search
None
See application file for complete search history.

(56) References Cited

U.S. PATENT DOCUMENTS

| | | | | |
|---|---|---|---|---|
| 5,714,140 | A * | 2/1998 | Strassmann | 424/85.1 |
| 6,124,257 | A | 9/2000 | Lezdey et al. | |
| 7,291,595 | B2 * | 11/2007 | Blanco | 514/20.3 |
| 8,071,551 | B2 * | 12/2011 | Shapiro | 514/20.3 |

FOREIGN PATENT DOCUMENTS

WO WO2005055956 6/2005

OTHER PUBLICATIONS

Lu et al. alpha1-antitrypsin Gene Therapy Modulates Cellular Immunity and Efficiently revents Type 1 Diabetes in Nonobese Diabetic Mice. Human Gene Therapy. Jun. 2006. vol. 17, pp. 625-634.*
Greenbaum.Insulin resistance in type 1 diabetes. Diabetes Metab Res Rev, 2002. vol. 18, pp. 192-200.*
Ramlo-Halsted et al. The Natural History of Type 2 Diabetes: Practical Points to Consider in Developing Prevention and Treatment Strategies. Clinical Diabetes. Spring 2000. vol. 18, No. 2, pages.*
Xu et al. Diabetes Gene Therapy: Potential and Challenges, Current Gene Therapy, 2003, vol. 3, pp. 65-82.*
Sulochana et al. Effect of oral supplementation of free amino acids in type 2 diabetic patients—a pilot clinical trial. Med Sci Monit, 2002. vol. 8, No. 3, pp. CR131-CR137.*
Teckman. Lack of Effect of Oral 4-Phenylbutyrate on Serum Alpha-1-Antitrypsin in Patients with alpha-1-Antitrypsin Deficiency: A Preliminary Study. J Pediatric Gastroenterology and Nutrition. Jul. 2004, vol. 39, No. 1, pp. 34-37.*
Von et al. Type 2 diabetes in children and adolescents. Screening, diagnosis, and management. Mar. 2007, JAAPA, vol. 20, No. 3, pp. 51-54.*
Ip et al., An Update on Type 2 Didabetes in Youth From the National Diabetes Education Program. Pediatrics, 2004, vol. 114, pp. 259-263.*
Kurachi et al. Cloning and sequence of cDNA coding for alpha1-antitrypsin. PNAS USA, vol. 78, No. 11, pp. 6826-6830.*
Lewis et al., alpha1-Antitrypsin monotherapy prolongs islet allograft survival in mice. *PNAS*, vol. 102, No. 34, pp. 12153-12158, Aug. 23, 2005.
International Search Report and Written Opinion dated Jul. 25, 2008 for corresponding International Appln. No. PCT/US2007/078231.
European Search Report, Application No. 07853534.1-2107 / 2066174 PCT/US2007078231, dated Aug. 5, 2011, (pp. 1-8).
Herold et al., "Anti-CD3 Monoclonal Antibody in New-Onset Type 1 Diabetes Mellitus," *New England Journal of Medicine, The, Massachusetts Medical Society*, vol. 346, No. 22, pp. 1692-1698, May 30, 2002.
Lewis at al,, "Alpha 1-Antitrypsin Monotherapv Prolongs Islet Allograft Survival in Mice," *PNAS*, vol. 102, No. 34, pp. 12153-12158, Aug. 23, 2005.
Nielsen at al., "Pharmacology of Exenatide (Synthetic Exendin-4): A Potential Therapeutic for Improved Glycemic Control of Type 2 Diabetes," *Regulatory Peptides*, vol. 117, No. 2, pp. 77-88, Feb. 15, 2004.
Yang Xiao-Dong et al., "Effect of Tumor Necrosis Factor Alpha on Insulin-Dependent Diabetes Mellitus in NOD Mice.1. The Early Development of Autoimmunity and the Diabetogenic Process," *Journal of Experimental Medicine*, vol. 180, No. 3, pp. 995-1004, 1994.

(Continued)

*Primary Examiner* — Marcela M Cordero Garcia
(74) *Attorney, Agent, or Firm* — Fish & Richardson P.C.

(57) ABSTRACT

Methods and compositions for treating patients (e.g., patients who are insulin resistant, patients who have diabetes, or are at risk for developing diabetes) are disclosed herein. The methods can include administration of an a1 antitrypsin (AAT) polypeptide or an agent, such as a nucleic acid molecule or organic compound, that promotes the expression or activity of a1-antitrypsin.

55 Claims, 1 Drawing Sheet

(56) References Cited

OTHER PUBLICATIONS

Yazdani-Biuki et al., "Improvement of Insulin Sensitivity in Insulin Resistant Subjects During Prolonged Treatment with the Anti-TNF-Alpha Antibody Infliximab," *European Journal of Clinical Investigation*, vol. 34, No. 9, pp. 641-642, Sep. 2004.

S. Song et al., "Recombinant Adeno-Associated Virus-Mediated Alpha-1 Antitrypsin Gene Therapy Prevents Type I Diabetes in NOD Mice" *Gene Therapy* (2004) 11:181-186 Nature Publishing Group.

E. C. Lewis et al., "α1-Antitrypsin Monotherapy Prolongs Islet Allograft Survival in Mice" *PNAS* (Aug. 23, 2005) 102(34)12153-12158 The National Academy of the Sciences of the USA.

M. Hashemi et al., "Impaired Activity of Serum Alpha-1-Antitrypsin in Diabetes Mellitus" Article in Press *Diabetes Research and Clinical Practice* xxx (2006) xxx-xxx Elsevier Ireland Ltd. (available online at www.sciencedirect.com).

Y. Lu et al., "$\alpha_1$-Antitrypsin Gene Therapy Modulates Cellular Immunity and Efficiently Prevents Type 1 Diabetes in Nonobese Diabetic Mice" *Human Gene Therapy* (Jun. 2006) 17:625-634 Mary Ann Liebert, Inc.

P. Finotti, "The Role Played by Serine Proteases in the Development and Worsening of Vascular Complications in Type I Diabetes Mellitus" *Current Diabetes Reviews* (2006) 2:295-305 Bentham Science Publishers Ltd.

P. Finotti et al., "Alteration of Plasma Proteinase-Antiproteinase System in Type I Diabetic Patients. Influence of Sex and Relationship with Metabolic Control" *Diabetes Research and Clinical Practice* (1992) 18:35-42 Elsevier Science Publishers B. V.

M. Sandler et al. "Serum Alpha-1-Protease Inhibitor Activity and Pulmonary Function in Young Insulin-Dependent Diabetic Subjects" *Respiration* (1987) 52:281-289 S. Karger AG, Basel.

European Office Action; Application No. 07853534.1-2107; mailed Dec. 19, 2012; Applicant: Beth Israel Deaconess Medical Center, Inc.; 7 pages.

* cited by examiner

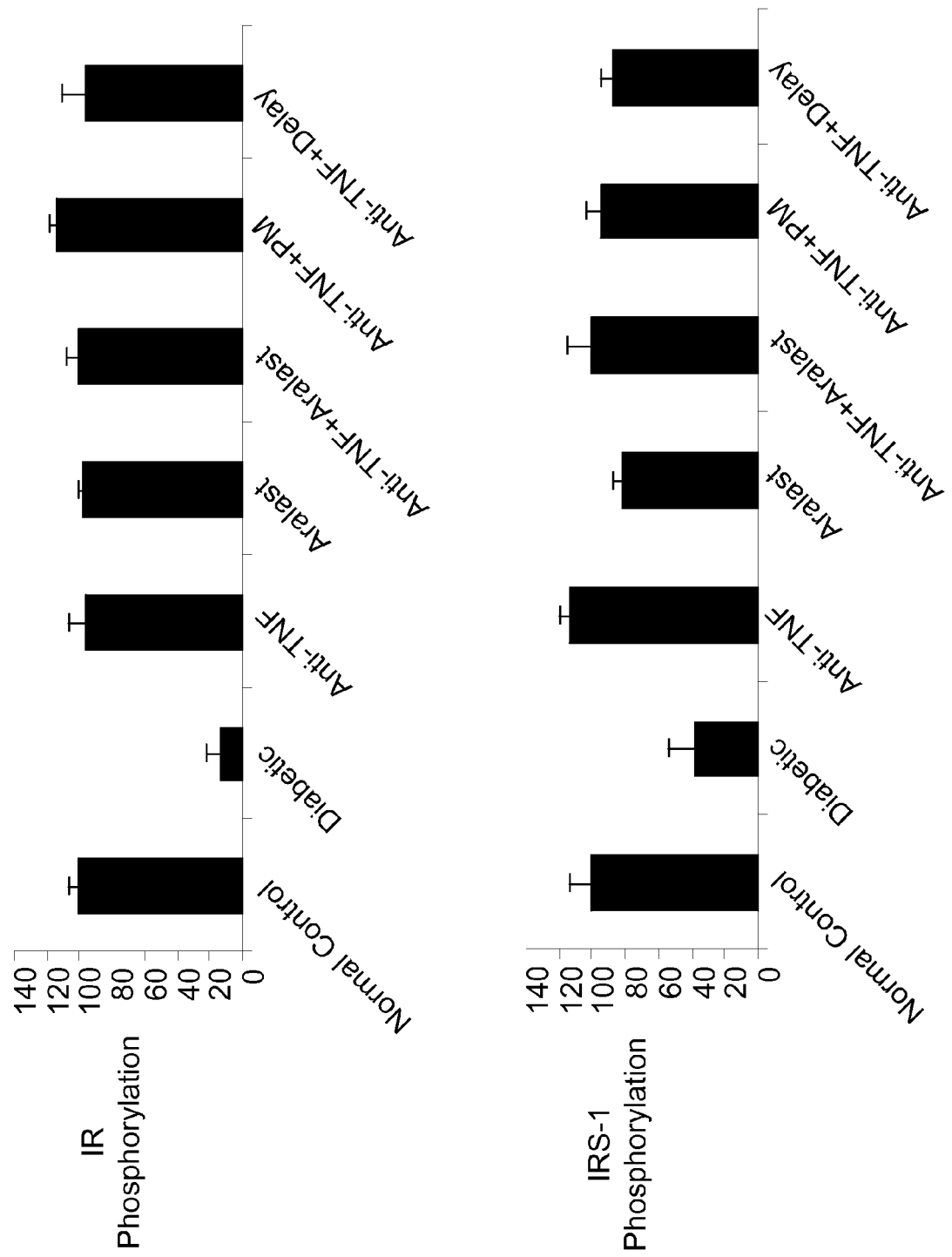

COMPOSITIONS CONTAINING α-1-ANTITRYPSIN AND METHODS FOR USE

CROSS REFERENCE TO RELATED APPLICATIONS

This application is a National Stage application filed under 35 U.S.C. §371 and claims the benefit under 35 U.S.C. §119(a) of International Application No. US2007/078231, filed on Sep. 12, 2007, which claims the benefit of priority under 35 U.S.C. §119(e) to U.S. Application No. 60/844,003, filed on Sep. 12, 2006, all of which are incorporated herein by reference in their entirety.

TECHNICAL FIELD

The present invention relates generally to the treatment of patients who are insulin resistant. These patients include those who have Type 2 diabetes, or who are at risk of developing Type 2 diabetes, and patients diagnosed as having metabolic syndrome. The treatment methods are varied and can include administration of an α1-antitrypsin (AAT) polypeptide or an agent, such as a nucleic acid molecule or organic compound, that promotes the expression or activity of α1-antitrypsin.

BACKGROUND

Diabetes is a very common disease that develops when the body does not produce enough, or appreciably any, insulin or cannot properly use or respond to insulin. There are two major types of diabetes. Type 1 diabetes is also known as insulin-dependent diabetes mellitus (IDDM) and results from insufficient insulin production. The onset of Type 1 diabetes occurs most often in children, adolescents, or young adults and is regarded as an autoimmune disease. Type 2 diabetes is known as noninsulin-dependent diabetes mellitus (NIDDM) and is the most common form of the disease, accounting for about 90% of all cases of diabetes. In many cases, Type 2 diabetes, in the initial phases, is characterized by a suboptimal response to insulin. Although insulin is produced, the ability of a given amount of insulin needed to effect a given decrease in blood glucose is increased. In Type 2, patients manifest a blunted blood glucose response to insulin, i.e., a state of insulin resistance. The causes of diabetes are not completely known, although both genetic and environmental factors, such as obesity and lack of exercise, increase the risk. There is also a form of diabetes that may develop during pregnancy (gestational diabetes), and a form of autoimmune diabetes that develops in adulthood, which is called latent autoimmune diabetes in adults (LADA) or slowly progressing autoimmune diabetes.

Type 1 diabetes is treated with insulin, although other treatments have been proposed and transplantation of insulin-producing islet cells from the pancreas has been tested. Non-pharmaceutical intervention is usually prescribed initially for Type 2 diabetes (e.g., diet modification, weight loss, and exercise). If this is not successful, patients are then generally treated with one of three different types of drugs: drugs that stimulate the release of insulin from the pancreas; drugs that increase a patient's sensitivity to insulin; and drugs that directly affect the circulating levels of glucose (e.g., drugs that decrease the production of glucose from the liver or increase its uptake by muscles). More specifically, a patient may be prescribed a sulfonylurea, an α-glucosidase inhibitor, metformin (GLUCOPHAGE™), or troglitazone (REZULIN™). In many cases, insulin is also used. After many years of living with type 2 diabetes, some patients manifest exhaustion of the insulin producing apparatus and thereby require insulin therapy.

Despite the progress in understanding and treating diabetes, none of the current treatment strategies are optimal, and there is a great need for better ways to treat patients who have diabetes or who are at risk of developing diabetes.

SUMMARY OF THE INVENTION

The present invention features, inter alia, methods of treating patients who are insulin resistant. Generally, the methods can be carried out by identifying a patient who is insulin resistant and administering to the patient a therapeutically effective amount of α1-antitrypsin (AAT; sometimes abbreviated A1AT), which is also referred to as α1-proteinase inhibitor. For example, one can administer an AAT polypeptide (e.g., a purified or recombinant AAT, such as human AAT) or a homolog, biologically active fragment, or other active mutant thereof. Alternatively, or in addition, one can administer an agent that promotes the expression or activity of an α1-antitrypsin (e.g., a gene encoding an α1 antitrypsin). While we describe insulin resistance and the patients amenable to treatment further below, we note here that patients who exhibit insulin resistance are not able to efficiently utilize insulin. Currently available tests can indicate whether a given patient is insulin resistant. For example, in an insulin tolerance test, insulin is administered and blood glucose is measured in response. If blood glucose levels do not fall as expected in response to the administered insulin, the patient is insulin resistant.

A patient who is insulin resistant can also be a patient who has been diagnosed as having Type 1 diabetes. In this circumstance, the patient is insulin deficient. Insulin production is compromised but it is not abolished. In addition, the patient is also insulin resistant, thereby preventing or impairing the residual mass of insulin producing cells to prevent hyperglycemia. The diagnosis of Type 1 diabetes can be based on one or more findings or indicators, such as hyperglycemia (i.e., a blood glucose level indicative of diabetes) with: (a) hypoinsulinemia; (b) other evidence of pancreatic β cell loss or functional insufficiency; (c) a normal or slightly impaired blood glucose response to insulin; (d) ketoacidosis; or (e) insulin dependence (i.e., a dependence on insulin to obtain blood glucose levels within, or closer to, a normal range (i.e., a range usually observed in healthy or non-diabetic individuals). Patients with Type 1 diabetes must take insulin. Otherwise, their health deteriorates rapidly.

Our statement that patients who are insulin resistant can have Type 1 diabetes and our statement that these same patients can be hyperglycemic and yet exhibit a normal blood glucose response to insulin may seem contradictory. As noted above, Type 1 diabetes is referred to as insulin-dependent diabetes mellitus because it has been historically understood as a condition that results when the β cells in the pancreatic islets of Langerhans do not produce sufficient insulin to facilitate cellular uptake of glucose from the blood. It remains true that Type 1 diabetes is indicated when blood glucose is elevated and the level of circulating insulin is abnormally low. It is also true that some patients with Type 1 diabetes may respond normally, or nearly normally, when exogenous insulin is administered, while others may also have an insulin resistant state. What our research has indicated, however, is that there is an insulin resistant component in early onset Type 1 diabetes, and insulin resistance may contribute to Type 1 diabetes even in non-obese patients. For example, our studies with new onset type 1 diabetic non-obese diabetic (NOD)

mice, the best available model for Type 1 diabetes, show an abnormal insulin tolerance test. This abnormality is seen in concert with reduction in both tyrosyl-phosphorylation of insulin receptor (IR) and the insulin receptor substrate-1 (IRS-1). Normal phosphorylation of both the IR and IRS-1 was restored by treatment with an α1-antitrypsin (Aralast™) (ARALAST™) or a TNF-α antagonist (see FIG. 1). This insulin resistance state is not abolished through normalization of blood glucose levels with intensive insulin therapy, and it is associated with molecular signs of subtle inflammation within fat and muscle, the primary sites for insulin driven disposal of blood glucose.

Insulin levels are reflected by the level of a protein called C-peptide (for connecting peptide). In the course of producing insulin, the body first produces proinsulin, which is subsequently cleaved into insulin and C-peptide. Thus, in attempting to distinguish patients who have Type 1 diabetes from patients who have Type 2 diabetes, a physician can assess C-peptide. Hypoinsulinemia, as seen in Type 1 diabetes, is reflected by a diminished level of C-peptide in circulating blood.

Any of the patients described herein can be human patients. In the past, Type 1 diabetes was far more prevalent in young people than Type 2 diabetes. Unfortunately the epidemic of obesity within our culture has led to many young obese individuals with type 2 diabetes. Youngsters with Type 2 diabetes are no longer rare. Moreover, an adult patient can develop late-onset Type 1 diabetes. Nevertheless, a patient's age or, more generally, whether the patient is a child, adolescent, or adult can be taken into consideration in the diagnostic process, as can the patient's family history.

Other insulin resistant patients are those diagnosed as having Type 2 diabetes. This diagnosis can be based on hyperglycemia with one or more of: (a) a normal or elevated level of insulin; (b) other evidence of pancreatic β cell maintenance; (c) a blunted blood glucose response to insulin; or (d) a family history of Type 2 diabetes. Our methods are applicable to treatment of insulin resistance and do not require frank diabetes. As with Type 1 diabetes, while insulin can be measured directly, a physician can assess insulin production by measuring C-peptide and, in some instances (e.g., where a patient has received exogenous insulin), C-peptide more accurately reflects insulin production. A normal level of insulin (i.e., a level within a range typically observed in healthy and/or non-diabetic patients) is reflected by a normal level of C-peptide (i.e. a level within a range typically observed in healthy and/or non-diabetic patients). Elevated C-peptide reflects elevated insulin. While the presence of normal or elevated levels of insulin indicate but do not prove that an adequate number of β cells are present and functional, one can look for other evidence that these insulin-producing cells are healthy (e.g., one can determine whether the patient is carrying anti-β cell antibodies). An insulin tolerance test can also be useful in diagnosing Type 2 diabetes. When a patient's response to insulin is blunted (i.e., when administered insulin does not bring about the expected reduction in blood glucose), it indicates that the patient's insulin responsive tissues, tissues responsible for insulin driven tissue disposal of blood glucose, are resistant to insulin, as occurs in Type 2 diabetes. The problem is not primarily insulin production, as is the case with Type 1 diabetes. As noted above, we have discovered a degree of insulin resistance in Type 1 diabetes.

The present methods are also useful in treating patients who are diagnosed as being at risk for developing Type 2 diabetes (e.g., as having a greater than average risk of developing Type 2 diabetes). This diagnosis can be based on one or more of the following findings: (a) impaired glucose tolerance with or without features of metabolic syndrome; (b) normal or impaired glucose tolerance with hyperinsulinemia; or (c) impaired glucose tolerance and a family history of Type 2 diabetes. Impaired glucose tolerance (IGT) is present when a patient has a blood glucose level that is higher than normal, but not high enough for the patient to be considered diabetic. IGT may also be referred to as borderline diabetes, pre-diabetes, or chemical diabetes. A specific population of patients known to be at risk for Type 2 diabetes is the population of female patients who have had gestational diabetes.

While we tend to use the term "impaired glucose tolerance" (IGT), one of skill in the art may also refer to patients as having impaired fasting glucose (IFG). The difference stems from the exact test used to diagnose patients (e.g., patients at risk of developing diabetes), and these tests are known in the art and described further below.

Patients who are diagnosed as having metabolic syndrome exhibit insulin resistance. In fact, metabolic syndrome is also referred to as the insulin resistance syndrome or Syndrome X. As noted above, one can consider the features of metabolic syndrome when determining whether a patient is at risk of developing Type 2 diabetes, as patients who have metabolic syndrome are more likely to develop Type 2 diabetes. Risk for Type 2 diabetes can be assessed without considering these features, however, and, while patients who exhibit features of metabolic syndrome do have a higher risk for diabetes, they also have a higher risk of developing other conditions, such as cardiovascular disease. Thus, one can assess and treat a patient who has metabolic syndrome as described herein, and one can do so with the aim of reducing the patient's risk of developing diabetes or any other undesirable condition associated with metabolic syndrome.

The features of metabolic syndrome include abdominal obesity, atherogenic dyslipidemia, a prothrombotic state, elevated blood pressure, and elevated levels of inflammatory cytokines. More specifically a patient may be diagnosed as having metabolic syndrome if they have two, three or more of: (a) an elevated waist circumference; (b) elevated triglycerides; (c) reduced high density lipoproteins (1-HDLs); (d) elevated blood pressure; and (e) elevated fasting glucose.

The invention also encompasses methods of treating patients who are at risk of developing Type 1 diabetes (e.g., patients who have a greater than average risk of developing Type 1 diabetes) or individuals with new onset Type 1 diabetes and low residual insulin production. These treatment methods can be carried out by identifying a patient who is at risk (e.g., a heightened risk) of developing Type 1 diabetes and administering to the patient a therapeutically effective amount of an α1-antitrypsin polypeptide or an agent that promotes the expression or activity of α1-antitrypsin. The patient who has been identified can be a patient who was diagnosed as being at risk of developing Type 1 diabetes on the basis of one or more of the following: (a) having a family history of Type 1 diabetes, with or without impaired glucose tolerance; or (b) having impaired glucose tolerance and evidence of pancreatic β cell loss or functional insufficiency. With respect to family history, a patient has an increased risk of developing Type 1 diabetes when they are a sibling of (e.g., an identical twin of) a patient who has Type 1 diabetes. Evidence of pancreatic β cell loss includes, as it does in the event of making any diabetes-related diagnosis, hypoinsulinemia and/or the presence of anti-β cell antibodies.

In any of the methods described herein, one can administer a therapeutically effective amount of an α1-proteinase inhibitor. For example, one can administer an α1-antitrypsin polypeptide, which may be a full-length α1-antitrypsin polypeptide (of human or other origin) or a biologically active fragment or mutant thereof. α1 proteinase inhibitors are commercially available for the treatment of AAT deficiencies, and include ARALAST™, PROLASTIN™, and ZEMAIRA™. As noted, the AAT polypeptide or the biologically active fragment or mutant thereof can be of human origin and can be purified from human tissue or plasma. Alternatively, it can be recombinantly produced. For ease of reading, we do not repeat the phrase "or a biologically active fragment or mutant thereof" after each reference to AAT. It is to be understood that, whenever a full-length, naturally occurring AAT can be used, a biologically active fragment or other biologically active mutant thereof (e.g., a mutant in which one or more amino acid residues have be substituted) can also be used. Similarly, we do not repeat on each occasion that a naturally occurring polypeptide (e.g., AAT) can be purified from a natural source or recombinantly produced. It is to be understood that both forms may be useful. Similarly, we do not repeatedly specify that the polypeptide can be of human or non-human origin. While there may be advantages to administering a human protein, the invention is not so limited.

Agents that promote the expression of α1-antitrypsin include nucleic acid molecules encoding a full-length, naturally occurring α1-antitrypsin polypeptide or a biologically active fragment or other mutant thereof. The nucleic acid molecules can include regulatory elements such as constitutively active or tissue-specific promoters to facilitate expression of the AAT-encoding sequence. Many suitable vectors, including plasmid and viral vectors are known in the art and can be used to deliver the present nucleic acid molecules to patients. The nucleic acid molecules can also include sequences that serve as reporters or tags or sequences that increase the circulating half-life of an AAT polypeptide to which they are joined (e.g., a portion of an immunoglobulin (e.g., an Fc region) or an albumin (e.g., human albumin).

Agents that promote the activity of α1-antitrypsin include agents that promote the secretion of α1-antitrypsin (e.g., PBA).

The invention encompasses combination therapies. For example, patients can be treated with an α1-proteinase inhibitor (e.g., ARALAST™) and an anti-inflammatory agent (e.g., an agent that selectively inhibits TNFα or a moiety within the TNFα signaling pathway). For example, the agent that inhibits TNFα can be an anti-TNFα antibody, which may be a human, humanized, chimeric or single chain antibody. The antibody can also be a polyclonal or monoclonal antibody. Anti-TNFα antibodies that are currently available and can be used in the methods described herein include adalimumab (HUMIRA®) and infliximab (REMICADE®). These antibodies are currently prescribed for the treatment of rheumatoid arthritis or psoriatic arthritis. Other useful antibodies include CDP571, which is a humanized monoclonal anti-TNFα antibody; D2E7, which is a human anti-TNF monoclonal antibody; and CDP870 (certolizumab pegol), which is an anti-TNFα pegylated antibody fragment (FAb). CDP870 has been used in clinical trials for the treatment of rheumatoid arthritis and Crohn's disease.

Alternatively, or in addition, patients can be treated with an α1-proteinase inhibitor and, as an agent that selectively inhibits a moiety within the TNFα signaling pathway, a soluble TNFα receptor antagonist. Useful agents may be soluble and include a sufficient portion of the TNFα receptor to bind TNFα. These antagonists can include a heterologous portion (i.e., a non-TNFα receptor-related portion) that may increase the antagonist's circulating half-life. For example, the antagonists can include an immunoglobulin-like molecule, as is included in etanercept (ENBREL®). Etanercept (ENBREL®) per se can also be used. In other embodiments, the heterologous portion of the antagonist can be an albumin (e.g., human serum albumin) or polyethylene glycol. The antagonist can be a PEGylated soluble tumor necrosis factor type I (PEG-sTNF-RI) per se or can include or consist of the p55 portion of the receptor found in this antagonist (see, e.g., Edwards et al., *Adv. Drug. Delivery Res.* 55:1315-1336, 2003).

Alternatively, or in addition, patients can be treated with an α1-proteinase inhibitor and, as an agent that selectively inhibits a moiety within the TNFα signaling pathway, an inhibitor of TACE (TNFα converting enzyme).

Other useful TNFα inhibitors, any of which, or any combination of which, can be administered in connection with AAT, include agents that selectively inhibit TNFα expression, such as RNA molecules that mediate RNAi (e.g., a TNFα selective siRNA or shRNA) and antisense oligonucleotides. More specifically, one can administer a molecule that mediates RNAi (e.g., a short interfering nucleic acid (siNA), a short interfering RNA (siRNA), a double-stranded RNA (dsRNA), or a short hairpin RNA (shRNA) as described in published U.S. Patent Application No. 20050227935, the contents of which are incorporated herein by reference in their entirety. TNFα expression or activity can also be selectively inhibited by small organic or inorganic compounds (e.g., LMP420; Haraguchi et al., *AIDS Res. Ther.* 3:8, 2006), thalidomide or a thalidomide analog, or a phosphodiesterase type IV inhibitor. Where small organic compounds and pharmaceuticals such as thalidomide are used, a prodrug may also be used.

Alternatively, or in addition, patients can be treated with an antagonist of an inflammatory cytokine such as IL-1, IL-6, or IL-8. For example, anakinra (KINERET™) can be used to inhibit IL-1.

Other agents useful in the present methods (e.g., in combination with an AAT) include agonists of a glucagon-like peptide (GLP) receptor (e.g., GLP-1) or of an exendin receptor. For example, the agonist of the GLP receptor or the agonist of the exendin receptor can be exendin-3, exendin-4, or GLP-1(7-36)-amide.

Other agents useful in the present methods (e.g. in combination with an AAT) include CD3 antagonists (e.g., an anti-CD3 antibody).

The number of patients at risk for developing diabetes is substantial. In a cross-section of U.S. adults aged 40 to 74, who were tested during the period 1988 to 1994, 33.8 percent had IFG, 15.4 percent had IGT, and 40.1 percent had pre-diabetes (IGT or IFG or both). Applying these percentages to the 2000 U.S. population, about 35 million adults aged 40 to 74 would have IFG, 16 million would have IGT, and 41 million would have pre-diabetes.

Other features and advantages of the present invention are described in the drawing, the detailed description, the examples, and the claims.

All cited patents, patent applications, and references (including references to public sequence database entries) are incorporated by reference in their entireties for all purposes. U.S. Provisional App. No. 60/844,003, filed Sep. 12, 2006, is incorporated by reference in its entirety for all purposes.

BRIEF DESCRIPTION OF THE DRAWING

FIG. 1 is a pair of bar graphs representing the results obtained from studies of insulin signaling in skeletal muscle. The upper graph charts insulin receptor (IR) phosphorylation and the lower graph charts insulin receptor substrate-1 (IRS-1) phosphorylation in control, diabetic, and treated animals.

DETAILED DESCRIPTION

The compositions and methods described herein can be used to treat patients who are insulin resistant. These insulin resistant patients include those who have Type 2 diabetes (a condition understood to be associated with insulin resistance), individuals who are at risk of developing Type 2 diabetes, and patients diagnosed as having metabolic syndrome. The patients also include insulin deficient patients with Type 1 diabetes, marginal islet function, and insulin resistance.

We have found that a short course of AAT restores normoglycemia in new onset diabetic NOD mice—a daunting and clinically predictive model for Type 1 diabetes. Many agents have proven effective in preventing frank diabetes when given after early signs of autoimmunity are present, but very few of these agents are effective after the onset of hyperglycemia. Some, but not many, of these agents work after establishment of significant islet cell damage in advance of elevated blood glucose levels.

We propose AAT and AAT-inclusive therapeutic regimes for the treatment of new onset diabetes. For example, AAT and AAT-inclusive therapeutic regimes can be used to treat patients in whom laboratory tests reveal evidence of diabetogenic autoimmunity. That evidence currently includes islet-specific autoantibodies, and relevant T cell assays are being developed. As noted here, patients amenable to treatment include those that exhibit pancreatic β cell loss or functional insufficiency. These patients, particularly when they also exhibit impaired glucose tolerance, are at risk of developing Type 1 diabetes or are at the inflection point between a diabetic and non-diabetic state. One of ordinary skill in the art will recognize that there is a progression of events associated with oncoming illness and that patients can be treated at varying points along the continuum.

While the present compositions and methods are clearly contemplated for use in human patients, the invention is not so limited. The compositions and methods can be used in veterinary settings as well (e.g., to treat a domesticated animal such as a dog, cat, or horse).

The methods can, but do not necessarily, include steps of determining whether or not a patient is insulin resistant or has another condition described herein as being treatable with AAT or as otherwise described herein. Thus, the methods may, but do not necessarily, include a step in which a patient is identified and a step in which one or more therapeutic agents are administered. Identifying the patient can begin with a physical examination and consideration of the patient's symptoms. Patients who have acquired diabetes, or who are in the process of becoming diabetic, often complain of polyphagia, polydipsia, and polyuria. They may also complain of nausea, with or without vomiting. While patients who are insulin resistant or who are prediabetic may have no symptoms of diabetes, there are severe forms of insulin resistance that produce dark patches on the skin, usually at the back of the neck or around the neck. There may also be dark patches on the elbows, knees, knuckles, and armpits. This condition is called acanthosis nigricans. With any such symptoms, and further in consideration of the patient's family history, a physician or other health care professional may order blood tests, such as those described below, to assess the amount of sugar and insulin in the patient's blood Patients who are insulin resistant are not able to utilize insulin as they should. Currently available tests can indicate whether a given patient is insulin resistant. For example, to test insulin tolerance, a patient is given insulin, and their response is assessed by monitoring resulting changes in blood glucose levels. The question is whether blood glucose falls as one would expect for a healthy or non-diabetic patient or whether it remains high or higher than expected. Where blood glucose does not fall as one would expect, the patient is exhibiting insulin resistance. Various specific tests are known in the art and can be used to detect insulin resistance. For example, 0.1 unit/kg of crystalline insulin can be injected intravenously and blood samples can be drawn to measure glucose at about −5, 0, 3, 5, 10, and 15 minutes relative to the time of the injection. Insulin resistance can be calculated using the slope of descending blood glucose levels (SI1). In one study, healthy women were found to have an SI1 of 0.58 (the range was 0.53-0.63) (Sin et al., *Revista medica de Chile* 124:931-937, 1996). The researchers conducting this study concluded that the insulin tolerance test is a good method for measuring insulin resistance and has a good correlation with the frequently sampled intravenous glucose tolerance test.

Because the insulin tolerance test can cause some patients to experience unpleasant symptoms, a "short" insulin tolerance test can also be used. This test is particularly useful when large numbers of subjects require screening or when the patient's fasting glucose level is normal. The "short" test employs a lower dose of insulin than the conventional 0.1 unit/kg bolus injection or the infusion administered in a euglycaemic hyperinsulinaemic clamp, and measurements are recorded for a shorter period of time. For example, one can measure insulin sensitivity using the slope of arterialized blood glucose concentration from about 3 to 15 minutes after an intravenous bolus of short-acting insulin (0.05 units/kg body weight). See Gelding et al., *Clin. Endocrinol. (Oxf.)* 40:611-615, 1994).

Patients who have untreated diabetes, whether of Type 1 or Type 2, are hyperglycemic (i.e., they exhibit, preferably on more than one occasion, a blood glucose level elevated to a level typically seen in diabetic patients). Blood glucose levels can be assessed in various ways. For example, a patient can be subjected to a glucose tolerance test. This test is well known and routinely performed. The patient fasts before a zero time (baseline) blood sample is drawn. Blood is then drawn at least one other time after the patient consumes a standardized high glucose-containing drink. The intervals and number of samples taken can vary according to the purpose of the test. For simple diabetes screening, the most important sample is generally considered to be one obtained two hours after the glucose has been consumed. However, additional samples may be taken at several different times (e.g., 30 minutes, one hour, two hours, and three hours) after the glucose has been consumed. The person being tested starts the test in a fasting state, having no food or drink except water, usually for at least the past eight hours (e.g., the past 10 to 16 hours or the past 8 to 14 hours). After the initial blood sample is drawn, the patient is given glucose, usually in the form of a drink (typically 1.75 grams of glucose per kilogram of body weight, to a maximum dose of 75 g; pregnant women may be given more). Blood samples are drawn again at varying intervals (e.g., as noted above). Certain activities, such as smoking, are known to affect the outcome, and patients should be advised to avoid those activities.

In a non-diabetic person, the glucose levels in the blood rise following drinking the glucose-containing drink, but then fall quickly back to normal because insulin is produced in response to the glucose, and the insulin has its normal effect of lowing blood glucose. In a diabetic patient, glucose levels rise higher than normal after drinking the glucose drink and come down to normal levels much more slowly because insulin is either not produced (which indicates Type 1 diabetes) or the patient's cells are insulin resistant (which indicates Type 2 diabetes).

One of ordinary skill in the art will be able to interpret the results of a glucose tolerance test, including the oral glucose tolerance test just described. The following information is provided for guidance, and is not intended to limit the scope of the invention.

A patient's fasting plasma glucose should be below 6.1 mmol/l (110 mg/dl). Fasting levels between 6.1 and 7.0 mmol/l (110 and 126 mg/dl) are borderline. These patients can be described as having an impaired fasting glucose level, and may be at risk of developing Type 1 or Type 2 diabetes. Fasting levels that are repeatedly at or above 7.0 mmol/l (126 mg/dl) are diagnostic of diabetes. These patients can be described as hyperglycemic. The 2-hour glucose level should be below 7.8 mmol/l (140 mg/dl). Levels between this and 11.1 mmol/l (200 mg/dl) indicate impaired glucose tolerance. As noted herein, patients who exhibit impaired glucose tolerance are at risk for developing diabetes. The diabetes may be Type 2 diabetes or, where the patient has a family history of Type 1 diabetes and/or evidence of pancreatic β cell loss, the risk is higher for Type 1 diabetes. Glucose levels above 11.1 mmol/l (200 mg/dl) at the 2-hour mark confirm hyperglycemia and a diagnosis of diabetes. For convenience, these figures are presented in the Table below.

wish to test for features classically associated with one form or the other. One of these features is the circulating level of insulin. Thus, before treating a patient, one may determine whether that patient has hyperglycemia and hypoinsulinemia (indicating Type 1 diabetes) or hyperglycemia and a normal or elevated level of insulin (hyperinsulinemia, indicating Type 2 diabetes).

A currently available laboratory test used to distinguish Type 1 from Type 2 diabetes is the C-peptide test, which detects the amount of insulin being produced in the body. Insulin resistance, determined by an insulin tolerance test can also be used, with a lack of insulin resistance, in the context of that test, suggesting Type 1 diabetes. More specifically, low or absent C-peptide levels indicate that insulin production is diminished or non-existent. Levels below the normal range of 0.5 to 3.0 ng/ml of plasma means that insulin production has slowed down abnormally.

In addition to a lack of insulin production, one can look for other evidence of pancreatic p cell loss or functional insufficiency in patients who have Type 1 diabetes. These patients may exhibit, for example, antibodies against some component of an islet cell. The primary antibodies found in 90% of Type 1 diabetics are against islet cell cytoplasmic proteins. These antibodies have been termed ICCAs (islet cell cytoplasmic antibodies). In non-diabetics, the frequency of ICCAs is only 0.5%-4%. The presence of ICCAs is a highly accurate predictor of future development of IDDM. Thus, one

| Glucose levels Venous | 1999 WHO Diabetes criteria - Interpretation of Oral Glucose Tolerance Test | | | | | | | |
|---|---|---|---|---|---|---|---|---|
| | NORMAL | | Impaired Fasting Glycaemia (I.F.G.) | | Impaired Glucose Tolerance (I.G.T.) | | Diabetes Mellitus (D.M.) | |
| Plasma | Fasting | 2 hrs | Fasting | 2 hrs | Fasting | 2 hrs | Fasting | 2 hrs |
| (mmol/l) | <6.1 | <7.8 | ≥6.1 & <7.0 | <7.8 | <7.0 | ≥7.8 | ≥7.0 | ≥11.1 |
| (mg/dl) | <110 | <140 | ≥110 & <126 | <140 | <126 | ≥140 | ≥126 | ≥200 |

While glucose is frequently administered orally, it may be given intravenously. Intravenous administration is indicated when a physician suspects early insulin secretion abnormalities in prediabetic states.

A woman has gestational diabetes when she is pregnant and has any two of the following: a fasting plasma glucose of more than 105 mg/dl, a 1-hour glucose level of more than 190 mg/dl, a 2-hour glucose level of more than 165 mg/dl, or a 3-hour glucose level of more than 145 mg/dl.

If the results of a glucose tolerance test indicate diabetes or a risk of diabetes, the test used can be repeated on a different day to improve one's confidence in the diagnosis. A combination of different tests can also be used. For example, if a blood test reveals a glucose level equal to or greater than 200 mg/dl at some point in an oral glucose tolerance test, the test can be repeated and/or one can test fasting plasma glucose levels.

In the fasting plasma glucose test, a person's blood glucose is measured once after a fast of eight to 12 hours. A person with normal blood glucose has a blood glucose level below 100. A person with impaired fasting glucose has a blood glucose level between 100 and 125 mg/dl. If the fasting blood glucose level rises to 126 mg/dl or above, the person has diabetes. As a preliminary matter, a plasma glucose test may be done even if the patient has not fasted.

While the methods described herein can be used to treat patients who have either Type 1 or Type 2 diabetes, one may may assess antibody content in the course of diagnosing patients at risk of developing Type 1 diabetes. Whether a direct cause or an effect of islet cell destruction, the titer of the ICCAs tends to decline over time. Autoantibodies directed against islet cell-surface antigens (ICSAs) have also been described in as many as 80% of Type 1 diabetics. Similar to ICCAs, the titer of ICSAs declines over time. Some patients with Type 2 diabetes have been identified that are ICSA-positive. Antibodies to glutamic acid decarboxylase (GAD) have also been identified in over 80% of patients newly diagnosed with IDDM, and anti-GAD antibodies decline over time in Type 1 diabetics. The presence of anti-GAD antibodies is a strong predictor of the future development of IDDM in high-risk populations. Anti-insulin antibodies have been identified in IDDM patients and in relatives at risk for developing IDDM. These antibodies are detectable even before the onset of insulin therapy in Type 1 diabetics, and have been found in an estimated 40% of young children with IDDM.

Yet another feature one can assess is a patient's response to insulin. A normal or slightly impaired blood glucose response to insulin indicates Type 1 diabetes while a blunted response indicates Type 2 diabetes. The insulin tolerance test was described above in the context of insulin resistance.

Diabetic ketoacidosis (DKA) is one consequence of severe, uncontrolled diabetes mellitus. As it results from a relative deficiency of insulin, it is an indicator of Type 1 diabetes. DKA can be present prior to diagnosis and may aid in diagnosis, but it may also occur after diagnosis as an indication that the therapeutic regime is inappropriate or has not been well followed. For example, DKA can occur when a patient fails to take the insulin prescribed. Insulin requirements may rise due to physiologic stress (e.g., an infection), which in turn causes the release of catecholamines, glucagon, and cortisol.

Insulin dependence is also an indicator of Type 1 diabetes. When a patient is insulin dependent, they exhibit a dependence on insulin to obtain blood glucose levels within, or closer to, a normal range (i.e., a range usually observed in healthy or non-diabetic individuals)). Currently, patients with Type 1 diabetes must take insulin.

While many features of Type 2 diabetes have been reviewed above, we reiterate that the present methods can include identifying, providing, or recognizing a patient with Type 2 diabetes based on the presence of hyperglycemia with one or more of: (a) a normal or elevated level of insulin; (b) other evidence of beta cell maintenance (e.g., a lack of anti-islet cell antibodies); (c) a blunted blood glucose response to insulin; and (d) a family history of Type 2 diabetes. With respect to treatment of a patient who is at risk for developing Type 2 diabetes (e.g., a patient whose risk is determined to be elevated over the general public's risk or over that of an identified sub-group of the general public to which the patient belongs), the present methods can include identifying, providing, or recognizing a patient with:
(a) impaired glucose tolerance, with or without features of metabolic syndrome; (b) normal or impaired glucose tolerance with hyperinsulinemia; and/or (c) impaired glucose tolerance with a family history of Type 2 diabetes. For example, the patient may have a blood glucose level that is elevated but not yet in the diabetic range and a C-peptide level within or above an appropriate normal range. Blood glucose levels and C-peptide levels are generally described above.

A test that can be performed to identify any insulin resistant patient is the Mal1 test. Accordingly, the present methods can include a step of identifying, providing, or recognizing a patient who is insulin resistant, or at risk of becoming so, on the basis of this test. Mal1 transcripts or a Mal1 protein can be detected in a tissue sample obtained from the patient. Even a small increase (e.g., an increase of at least 5% in the level of Mal1 transcripts or proteins) in the tissue sample compared to an appropriate control tissue indicates that the patient is, or is at risk of, developing insulin resistance. The Mal1 transcript can include SEQ ID NO:4 or the complement thereof as disclosed in U.S. Pat. No. 7,056,662, the content of which is hereby incorporated by reference in its entirety.

Mal1 is a fatty acid binding protein (FABP). Proteins in this family of small cytoplasmic proteins function to traffic lipids within cells. The gene encoding Mal1 is upregulated in multistage skin carcinogenesis, and the gene product is expressed in adipocytes as well as other cell types such as macrophages. As noted above, increased expression of Mal1 can be used to identify patients amenable to treatment as described herein. In addition, a Mal1 inhibitor can be used in combination with any of the therapeutic regimes described herein. For example, a Mal1 inhibitor can be administered with an AAT and/or an anti-inflammatory agent such as a TNFα inhibitor. Decreasing Mal1 expression or activity inhibits the development of obesity, insulin resistance, diabetes, dyslipidemia, and atherosclerosis. The Mal1 inhibitor can inhibit transcription of endogenous Mal1 by, for example, binding to a cis-acting regulatory sequence of the Mal1 gene and decreasing Mal1 transcription. Alternatively, the compound can be one that inhibits translation of Mal1 mRNA into a Mal1 gene product (e.g., an antisense nucleic acid complementary to a sufficient portion of Mal1 mRNA). Nucleic acids that produce antisense nucleic acids can also be used and can be driven by, for example, adipocyte- or macrophage-specific promoters).

The metabolic syndrome is characterized by a group of metabolic risk factors, some combination of which (e.g., two, three, or more) are manifest in one person. The identifying features include excessive weight or obesity, particularly abdominal obesity (i.e., excessive fat tissue in and around the abdomen); atherogenic dyslipidemia; hypertension; insulin resistance and/or glucose intolerance; a prothrombotic state; and a proinflammatory state. Atherogenic dyslipidemia refers to a blood fat disorder that fosters plaque buildup in arterial walls. Dyslipidemia can occur, for example, when a patient has high levels of triglycerides, low levels of HDL ("good") cholesterol, and high levels of LDL ("bad") cholesterol. Hypertension (or elevated blood pressure) strongly associates with obesity and commonly occurs in insulin resistant patients. Hypertension is therefore commonly listed among metabolic risk factors. Although some investigators believe that hypertension is less "metabolic" than other metabolic syndrome components, there seems to be a consensus that hypertension should be considered a risk factor for metabolic syndrome. A prothrombotic state is any condition that predisposes a patient to venous or arterial thrombosis. For example, a patient may have high levels of fibrinogen or plasminogen activator inhibitor-1 (PAI-1) in the blood. A proinflammatory state is present when C-reactive protein (or CRP, not to be confused with C-protein) is elevated in the blood. There is a connection between obesity and the proinflammatory state because excess adipose tissue releases inflammatory cytokines that may elicit higher CRP levels. Prothrombotic and proinflammatory states may also be metabolically interconnected. More specifically, in assessing a patient for metabolic syndrome, one can look for an elevated waist circumference (40 inches (102 cm) or more in men; 35 inches (88 cm) or more in women); triglycerides equal to or greater than 150 mg/dL; HDL cholesterol at less than 40 mg/dL in men and less than 50 mg/dL in women; a blood pressure elevated to 130/85 mm Hg or more; and an elevated fasting glucose equal to, or greater than, 100 mg/dL. Additional discussion of the features of metabolic syndrome is available in the scientific literature (see, e.g., Grundy et al. (*Circulation* 109:433-438, 2004). One can also consult the criteria proposed by the National Cholesterol Education Program (NCEP) Adult Treatment Panel III (ATP III) (Grundy et al., supra) and the American Heart Association and the National Heart, Lung, and Blood Institute recommendations. Other conditions associated with the syndrome include physical inactivity, aging, hormonal imbalance and genetic predisposition.

Patients diagnosed as having metabolic syndrome are at increased risk of not only Type 2 diabetes, but also of coronary heart disease and other diseases related to plaque buildup in arterial walls (e.g., cerebrovascular accident (CVA or "stroke") and peripheral vascular disease).

Patients who are not insulin resistant but who are at risk of developing Type 1 diabetes can also be treated by the present methods. While many features of Type 1 diabetes have been reviewed above, we reiterate that the present methods can include identifying, providing, or recognizing a patient at risk of developing Type 1 diabetes based on: (a) a family history of Type 1 diabetes, with or without impaired glucose tolerance and/or (b) impaired glucose tolerance and evidence of pancreatic β cell loss or functional insufficiency.

The term "secondary" diabetes has been used to refer to elevated blood sugar levels from another medical condition (i.e., a condition other than diabetes per se). Secondary diabetes can develop, for example, when the pancreatic tissue responsible for the production of insulin is absent because it is destroyed by a disease other than diabetes, such as chronic pancreatitis, trauma, or surgical removal of the pancreas. Diabetes can also result from other hormonal disturbances, such as excessive growth hormone production, as occurs in acromegaly, and Cushing's syndrome. In acromegaly, a pituitary gland tumor at the base of the brain causes excessive production of growth hormone, leading to hyperglycemia. In Cushing's syndrome, the adrenal glands produce an excess of cortisol, which promotes blood sugar elevation. In addition, certain medications may worsen diabetes control, or unmask latent diabetes. This is seen most commonly when steroid medications (corticosteroids, including prednisone and cortisone) are taken. and also with medications used in the treatment of HIV infection (the virus associated with ARC and AIDS). Patients who have secondary diabetes, or who are at risk of developing secondary diabetes, can be treated as described herein (e.g., with an AAT or with an AAT and an anti-inflammatory agent (e.g., a TNFα inhibitor) and/or a Mal1 inhibitor). As with other patient populations described herein, the present methods may or may not including a step of identifying (e.g., diagnosing) a patient who has secondary diabetes or who is at risk of developing secondary diabetes. The methods can encompass treatment without reference to diagnosis.

The treatment regimes require administration of AAT, a biologically active fragment or other mutant thereof, or an agent that promotes the expression or activity of AAT.

AAT is a protein found in plasma which, due to its structural and functional properties, is classified in the super family of serpins (serine protease inhibitors). It is because of its serine protease inhibiting effect that AAT is also known as α1-proteinase inhibitor. As AAT is responsible for approximately 90% of the tryptic inhibition capacity of normal plasma, it is also termed major plasma serpin. AATs inhibitory activity relative to elastase is particularly important.

AAT is primarily a protective protein; it protects cells from liberated proteolytic enzymes. It is synthesized in the liver and secreted into plasma, where it has a half life of approximately six days. The normal concentration of AAT in plasma is about 1.3 WI.

Human AAT is a single-chain polypeptide of 394 amino acid residues with three glycosylation positions at the asparagine residues of positions 46, 83 and 247. Sialysation is described by Carrell et al. (*Nature* 298:329-334, 1982). There are at least two plasma forms of AAT. In one form, the five most N-terminal amino acid residues are removed. Substantial changes have been found in the relative proportion of the various isoforms in the event of inflammation and in response to estrogen (see Patterson, *Comp. Biochem. Physiol.* 100: 439-454, 1991).

AAT inhibits serine proteases by forming complexes with the proteases that block their activity. AAT itself is inhibited by liberated radicals that form in the course of inflammation. When AAT is blocked in the immediate vicinity of the inflammation, proteases such as elastase and cathepsin G are more fully available to attack any bacterial cells that may be causing the inflammation. One place where AAT inactivation can be detrimental, however, is in the lungs. If AAT, which helps protect the surface of the lungs, particularly in the lower respiratory tract, is compromised (e.g., by genetic deficiency or free radicals contained within cigarette smoke), the lung tissue can be damaged and emphysema may result or be exacerbated. Thus, AAT has been developed as a therapy for the treatment of emphysema (see our discussion below regarding ARALAST™). α1-proteinase inhibitor also inhibits human elastases in the pancreas and in leukocytes. See Pannell et al, *Biochemistry* 13:5339, 1974; Johnson et al., *Biochem. Biophys. Res. Commun.* 72:33, 1976; Del Mar et al, *Biochem. Biophys. Res. Commun.* 88:346, 1979; and Heimburger et al., *Proc. Int. Res. Conf. Proteinase Initiators.* 1st, 1-21, 1970.

More than 70 qualitative and quantitative variants of human AAT are known that are inherited as autosomal co-dominant alleles. As much as 10% of the European population may be carriers of a pathologic variant of AAT. The most remarkable pathologic results of AAT gene variance are degenerative lung disease and severe liver disease. Renal disorders, arthritis and malignancies are also suspected of being connected with an AAT gene variance.

In plasma, AAT occurs both in an active form and an inactive form (see, e.g., Pajdak et al., *Folia Histochemica et Cytobiologica,* 24:169-172, 1986).

There are a number of methods for producing AAT, some of which involve processing of various plasma fractions (Cohn fraction IV-1-precipitate or Kistler and Nitschmann Supernatant A or A+1) (Feldman and Winkelman, *Blood Separation and Plasma Fractionation*, Wiley-Liss, Inc., pp. 341-383, 1991). In more elaborate schemes, respective blood fractions are purified by means of DEAE cellulose (Basis et al., *Vopr. Med. Khim.* 33:54-59, 1987), treated with affinity chromatographic materials, or with cation exchanger chromatographic materials (EP-0 698 615-A1). Basis et al. describe a method for purifying AAT by ammonium sulfate precipitation of plasma and subsequent DEAE cellulose chromatography and hydroxylapatite chromatography. This method employs mercaptoethanol, which protects the protein against oxidation of S-containing groups. Following the hydroxylapatite chromatography, AAT is recovered in two fractions, but AAT and albumin are not completely separated.

Other methods have been developed to more completely separate inactive ATT from active ATT. For example, native, chromatographically purified AAT has been obtained that has a purity of at least or about 0.7 PU/mg protein (determined in an elastase inhibition assay) and a relative plasma AAT activity of at least or about 120% (see U.S. Pat. No. 6,974,792, the content of which is hereby incorporated by reference in its entirety). These purification methods can be used to obtain AAT for use in the present methods relating to insulin resistance and diabetes (e.g., in treating a patient who has a sufficiently high risk of developing Type 1 diabetes to merit treatment). Briefly, one can prepare an AAT isomer having a pI of between 4.3 and 4.4 by a method including the steps of: (a) providing a starting material containing active and inactive ATT (e.g., a plasma fraction obtained from pooled human plasma); (b) providing a hydroxyapatite substrate; (c) passing the starting material over the hydroxyapatite substrate; and (d) eluting a biologically active AAT preparation having a pI of between 4.3 and 4.4. The method can further include a step of passing the biologically active AAT preparation over an anion exchange material in the presence of a detergent. In other methods, one can purify biologically active AAT by a process including the steps of: (a) providing an AAT-containing fraction from a human plasma pool; (b) adjusting the pH of the AAT-containing fraction to about 6.5; (c) absorbing the acidified AAT-containing fraction onto a chromatographic anion exchanger in the presence of a detergent; and (d) eluting the biologically active AAT from the chromatographic anion exchanger. The resulting AAT isomers can have pIs of between 4.3 and 4.4

Purified AAT can be combined with a physiologically acceptable diluent (e.g., an excipient). Pharmaceutical preparations can optionally include pharmaceutically acceptable auxiliary substances, such as buffers, stabilizers, adjuvants, antioxidants, and salts. Further, the preparations can be treated to inactivate any pathogens therein, and they may be provided in storage-stable forms (e.g., in a lyophilized form or as a deep-frozen solution). Other preparations can be formulated for intravenous administration or as an aerosol or spray (e.g., for mucosal application). The preparations may also be provided in association with liposomes or phospholipids or with other micro- or nano-particulates.

AAT is also commercially available. In practicing the present methods, one can use commercially available α1-protease inhibitors such as ARALAST™, PROLASTIN™, and ZEMAIRA™. The purity of these AAT-containing preparations has been evaluated using reverse phase and size exclusion chromatography high performance liquid chromatography (RP-HPLC and SEC-HPLC), capillary zone electrophoresis (CZE), sodium dodecyl sulfate polyacrylamide gel electrophoresis, sodium dodecyl sulfate capillary gel electrophoresis and Western blot analysis (Cowdin et al., Curr. Med. Res. Opin. 21:877-883, 2005). The identity of protein impurities was determined by immunonephelometry; functionality by calculating the ratio of mg active A1-P1 present (by anti-neutrophil elastase activity assay) to the mg antigenic A1-PI (by immunonephelometry); and normality of the A1-PI isoform pattern by isoelectric focusing (IEF). Three samples of ZEMAIRA™ and one sample each of ARALAST™ and PROLASTIN™ were available for analysis. ZEMAIRA™ had the highest specific activity. Using RP-HPLC analysis, ZEMAIRA™ averaged 99% purity, ARALAST™ 70% and PROLASTIN™ less than 62%. Using SEC-HPLC, ZEMAIRA™ was 95.98% monomeric, PROLASTIN™ 79.00% and ARALAST™ 63.55%. Prolastin PROLASTIN™ had lower activity/mg antigenic A1-PI than the other two products. A shift in isoforms in ARALAST™ was suggested by the results of CZE, and was confirmed by IEF (Cowdin et al., supra).

While AAT purified from human plasma is an effective and useful form of AAT, plasma supplies can be limited and there is the potential for viral contamination. Accordingly, AAT, or a biologically active fragment or mutant thereof can be recombinantly produced in either plant or animal cells. AAT can be obtained from plant cells, for example, by the methods disclosed in U.S. Pat. No. 6,127,145, the content of which is hereby incorporated by reference in its entirety. Monocot plant cells were transformed with an AAT coding sequence and cultivated under conditions allowing for protein expression and secretion. The nucleic acid sequence used can be codon-optimized for more efficient translation in plant cell cultures.

AAT can also be produced in, and purified from, the milk of a non-human transgenic animal such as a cow. A method for purifying human or other α1-proteinase inhibitors from a solution, which may be derived from the milk of a non-human transgenic animal is described in U.S. Pat. No. 6,194,553, and includes the steps of contacting the solution with a cation exchange substrate under conditions sufficient to bind non-transgenic α1-proteinase inhibitor contaminants to the substrate while not substantially binding the transgenic α1-proteinase inhibitor. The purified transgenic α1-proteinase inhibitor was reported to contain as little as 40 pg of non-α1-proteinase inhibitor-whey protein per mg total protein. The content of U.S. Pat. No. 6,194,553 is hereby incorporated by reference in the present application in its entirety.

As with other pharmaceutical agents, the salts and other derivatives of an AAT can be formed using conventional techniques. These salts and other derivatives can have activity that is comparable to that of a naturally occurring AAT or an enhanced property (e.g., better stability or activity). More specifically, one can prepare an alkali metal salt, an acid-addition salt, or an ester using methods such as those conventionally used to modify polypeptide-based therapeutics.

As noted, in addition to administering a biologically active and naturally occurring AAT polypeptide, one can administer a biologically active fragment or other mutant of AAT. The biologically active fragment can differ from a corresponding wild type AAT by as little as 1-5 amino acid residues at either the N- or C-terminus or at both the N- and C-terminus. Greater deletions may also be made, however. For example, the N-most terminal residue can be deleted; the two N-most terminal residues can be deleted; the three N-most terminal residues can be deleted; and so forth. As noted any N-terminal deletion (e.g., a deletion of 1-10 of the N-terminal amino acid residues) can be made together with any C-terminal deletion (e.g., a deletion of 1-10 of the C-terminal amino acid residues). The extent of the truncation can also be expressed as a percentage. In that event, the biologically active fragment can differ from a corresponding wild type AAT by at least 1-10%, at least 11-20%, at least 21-30%, or at least 31-40%. In this context, by "at least" X–Y % we mean at least X % but no more than Y %. For example, the biologically active fragment can include at least 75, 80, 85, 90, 95, or 99% of the consecutive amino acid residues of a corresponding wild type AAT. Other mutants of AAT in which deletions are made at positions other than the N- and/or C-terminus can also be used so long as they remain biologically active. For example, one can delete at least 1-5 or more (e.g., 10) consecutive or non-consecutive amino acid residues of an AAT. As with truncated fragments, the deletion can be expressed in terms of a percentage difference relative to a corresponding wild type AAT. For example, a biologically active mutant AAT can differ from a wild type AAT by at least 1-10%, at least 11-20%, at least 21-30%, or at least 31-40%. For example, the biologically active mutant can be at least 75, 80, 85, 90, 95, or 99% identical to a corresponding wild type AAT. The degrees of identity described above are relevant to other types of mutants as well. For example, a biologically active AAT mutant can, in addition to, or as an alternative to, a truncation or internal deletion, include one or more substitution mutations (e.g., a given number of amino acid residues, in accordance with the degree of identity set out above, can be replaced with one or more amino acid residues, some of which or all of which represent a conservative substitution). A biologically active AAT mutant can also include one or more additional residues (i.e. the AAT can include an insertion mutation). Of course, combinations of these types of variants can be included. For example, one could produce an AAT in which 1-5 of the N-terminal amino acid residues are deleted and 1-5 of the remaining residues are substituted with another amino acid residue. Below, we describe administration of AAT to a patient. This may be accomplished by administration of an AAT polypeptide per se or of a nucleic acid sequence that encodes the AAT. We note here that the nucleic acid can be one that encodes any of the biologically active AAT variant polypeptides.

AAT inhibits the enzymatic activity of neutrophil elastase, cathepsin G, proteinase 3, thrombin, trypsin, and chymotrypsin. Accordingly, one can examine any agent (e.g., a fragment of an AAT polypeptide, an AAT mutant polypeptide, or a small organic molecule) for its ability to inhibit the enzymatic activity of one or more of these enzymes. The agent can be examined further in an animal model (e.g., an animal model of diabetes) or in a clinical trial.

The term "identical," when used to describe two or more nucleic acids or two or more polypeptides means that the two or more nucleic acids or the two or more polypeptides have the same nucleotide or amino acid sequences, respectively. Where a certain percent identity is required between two nucleic acids or two polypeptides, the nucleotide sequences or the amino acid sequences, respectively, must have a sufficient number of identical residues to satisfy the required degree of identity. The sequences to be compared can be aligned for maximum correspondence over a comparison window or a designated region, and identity can be measured using BLAST or BLAST 2.0 sequence comparison algorithms with the program-recommended default parameters. Percentage identity can also be determined by manual alignment and visual inspection.

For sequence comparison, one sequence typically acts as a reference sequence to which test sequences are compared. When using a sequence comparison algorithm, the reference and test sequences are simply entered into a computer, subsequence coordinates are designated, if necessary, and sequence algorithm program parameters are designated. Default program parameters can be used, and it is on the basis of those parameters that the percent identity for the variant AAT sequences described herein are determined. The sequence comparison algorithm then calculates the percent sequence identity for the test sequences relative to the reference sequence, based on the program parameters.

A comparison window is a segment of any one of the number of contiguous positions along an AAT-encoding or AAT-related nucleic acid or polypeptide, which can extend to include the entire length of a naturally occurring or mutant AAT polypeptide or nucleic acid. Methods of alignment of sequences for comparison (e.g., sequences within a comparison window) are well known in the art. Optimal alignment of sequences for comparison can be conducted, for example, by the local homology algorithm of Smith & Waterman (*Adv. Appl. Math.* 2:482, 1981), by the homology alignment algorithm of Needleman & Wunsch (*J. Mol. Biol.* 48:443, 1970), by the search for similarity method of Pearson & Lipman (*Proc. Natl. Acad. Sci. USA* 85:2444, 1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds., 1995 supplement)).

An algorithm that is suitable for determining percent sequence identity as well as sequence similarity or homology are the BLAST and BLAST 2.0 algorithms, which are described in Altschul et al. (*Nuc. Acids Res.* 25:3389-3402, 1977) and Altschul et al. (*J. Mol. Biol.* 215:403-410, 1990), respectively. BLAST and BLAST 2.0 are used, with the parameters described herein, to determine percent sequence identity for the AAT-encoding and AAT-related (i.e., variant) nucleic acids and proteins that can be combined and administered for treating a patient as described herein. Software for performing BLAST analyses is publicly available through the National Center for Biotechnology Information (NCBI; URL address: http file type, www host server, domain name ncbi.nlm.nih.gov).

In the event one wishes to align more than two sequences (e.g., a reference sequence and two or more test sequences), the algorithm PILEUP can be used. PILEUP creates a multiple sequence alignment from a group of related sequences using progressive, pairwise alignments to show relationship and percent sequence identity. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, for example, version 7.0 (Devereaux et al., *Nuc. Acids Res.* 12:387-395 (1984).

There are also functional tests for substantial identity. For example, when two nucleic acid sequences are substantially identical, the two sequences or their two complements hybridize to each other under stringent conditions. Under stringent conditions, a probe will hybridize to its target subsequence (e.g., a sequence encoding a wild type AAT), typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times (and preferably more (e.g., about 10 times) the background hybridization level. Exemplary stringent hybridization conditions can be as follows: 50% formamide, 5×SSC, and 1% SDS, with incubation at 42° C. or 5×SSC, 1% SDS, with incubation (for hybridization) at 65° C., followed by washing in 0.2×.SSC and 0.1% SDS at 65° C.

Those of ordinary skill will recognize that alternative hybridization and wash conditions can be utilized to provide conditions of similarly high stringency.

The fragments and other mutants of AAT described above have been referred to as biologically active and by that, we mean that the fragment or other mutants retain sufficient activity to be therapeutically useful (i.e., useful in treating a patient as described herein). To begin to determine therapeutic utility, one can administer the AAT fragment or other mutant to an NOD mouse. More specifically, one can administer the AAT fragment or other mutant under the circumstances in which Aralast™ was administered in the Examples below and then examine the animals' blood glucose levels. A biologically active fragment or other mutant is therapeutically useful when it promotes normoglycemia. Of course, prior to approval by the Food and Drug Administration and administration to human patients generally, such fragments or other mutants must be examined in human clinical trials. If desired, other assays can be carried out in cell culture or in vitro (e.g., one can test an AAT's activity against elastase by methods known in the art) to gather data relevant to biological activity.

1-AZT is a misfolded but functionally active mutant of AAT (Burrows et al., *Proc. Natl. Acad. Sci. USA* 97:1796-1801, 2000). 1-AZT can be used in the present compositions and methods.

Other useful variants of AAT include those that have a sequence that is identical to a naturally occurring, wild type AAT but are post-translationally modified in a way that differs from the naturally occurring, wild type AAT. For example, due to the cell type in which an AAT is produced, it may be glycosylated differently. Fragments and other mutants may also exhibit varying post-translational modifications (e.g., glycosylation) when recombinantly produced in varying cells types (e.g., in a bacterial cell such as an *E. coli* vs. a eukaryotic cell).

As noted, instead of, or in addition to, administering AAT or one of the variants of AAT described herein, one can administer an agent that promotes the expression or activity of AAT. The agent that promotes expression can be a genetic construct encoding AAT or one of the variants of AAT described herein. For ease of reading, we do not continue to repeat the phrase "or one of the variants of AAT described herein. Where reference is made to a nucleic acid encoding AAT it is to be understood that the nucleic acid may also encode any biologically active variant of AAT (e.g., the fragments or other mutants described above).

A variety of expression constructs can be used to express an AAT-encoding nucleic acid in a cell (e.g., in a cell (e.g., an autologous cell) that is transfected in culture or a cell in vivo). Adeno-associated viral (AAV) vectors have been used to express the human AAT gene from either the cytomegalovirus (CMV) promoter or the human elongation factor 1-alpha promoter (see Song et al., *Proc. Natl. Acad. Sci. USA* 95:14384-14388, 1998). Accordingly, viral vectors, such as AAV vectors, and promoters, such as CMV, can be used to deliver AAT-encoding nucleic acid sequences to cells in culture, from which AAT may then be purified, or to deliver AAT-encoding nucleic acid sequences to patients in the context of the present methods. The regulatory sequence naturally associated with AAT can also be used. For example, one can incorporate a KpnI-KpnI fragment containing the promoter region, the first non-coding exon and the 5' portion of intron 1 of AAT (the sequence of which is given by Long et al., *Biochemistry* 23:4828, 1984), or a portion thereof, into a vector such as pUC18 (Yanisch-Perron et al, *Gene* 33:103, 1985).

Other plasmids can also be used. For expression in prokaryotic hosts, for example, suitable plasmid vectors include pBR322 (available from the American Type Culture Collection (ATCC) (Manassas, Va.)(No. 37,017)), phGH107 (ATCC No. 40,011), pBO475, pS0132, pRIT5, any vector in the pRIT20 or pRIT30 series (Nilsson and Abrahmsen, *Meth. Enzymol.*, 185:144-161, 1990), pRIT2T, pKK233-2, pDR540 and pPL-λ. Prokaryotic host cells that can be used with the exemplary expression vectors just described (as well as others) include *E. coli*. For example, one can express an AAT in *E. coli* K12 strain 294 (ATCC No. 31,446), *E. coli* strain JM101 (Messing et al., *Nucl. Acids Res.* 9:309, 1981), *E. coli* strain B, *E. coli* strain χ1776 (ATCC No. 31,537), *E. coli* c600 (Appleyard, *Genetics* 39:440, 1954), *E. coli* W3110 (F-, gamma-, prototrophic, ATCC No. 27,325), *E. coli* strain 27C7 (W3110, tona, phoa E15, (argF-lac)169, ptr3, degP41, ompT, kanr) (U.S. Pat. No. 5,288,931; ATCC No. 55,244). Other useful prokaryotic host cells include *Bacillus subtilis, Salmonella typhimurium, Serratia marcesans*, and *Pseudomonas* species.

In addition to prokaryotes, eukaryotic organisms, such as yeasts, or cells derived from multicellular organisms can be used as host cells. For expression in yeast host cells, such as common baker's yeast or *Saccharomyces cerevisiae*, suitable vectors include episomally replicating vectors based on the 2-micron plasmid, integration vectors, and yeast artificial chromosome (YAC) vectors. For expression in insect host cells, such as Sf9 cells, suitable vectors include baculoviral vectors. For expression in plant host cells, particularly dicotyledonous plant hosts, such as tobacco, suitable expression vectors include vectors derived from the Ti plasmid of *Agrobacterium tumefaciens*.

Vertebrate host cells can also be used. Examples of useful mammalian host cells include monkey kidney CV1 line transformed by SV40 (COS-7, ATCC CRL 1651); human embryonic kidney line (293 or 293 cells subcloned for growth in suspension culture (Graham et al., *J. Gen Virol.* 36:59, 1977); baby hamster kidney cells (BHK, ATCC CCL 10); Chinese hamster ovary cells/-DHFR(CHO, Urlaub and Chasin, *Proc. Natl. Acad. Sci. USA* 77:4216, 1980); mouse sertoli cells (TM4, Mather, *Biol. Reprod.* 23:243-251, 1980); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL51); TRI cells (Mather et al., *Annals N.Y. Acad. Sci.* 383:44-68, 1982); MRC 5 cells; FS4 cells; and the cells of a human hepatoma cell line (Hep G2).

For expression in mammalian cells, including mammalian host cells in culture, useful vectors include vectors derived from SV40, vectors derived from cytomegalovirus such as the pRK vectors, including pRK5 and pRK7 (see Suva et al., *Science* 237:893-896, 1987; EP 307,247 (Mar. 15, 1989); and EP 278,776 (Aug. 17, 1988), vectors derived from vaccinia viruses or other pox viruses, and retroviral vectors such as vectors derived from Moloney's murine leukemia virus (Mo-MLV). Modified vaccinia Ankara vectors can also be used.

Optionally, the nucleic acid encoding the AAT of interest is operably linked to a secretory leader sequence resulting in secretion of the expression product by the host cell into the culture medium or from a cell in vivo. The leader sequence can be one naturally associated with AAT or a heterologous sequence. Examples of heterologous secretory leader sequences include stII, ecotin, lamB, herpes GD, lpp, alkaline phosphatase, invertase, and alpha factor leader sequences. Also suitable for use is the 36 amino acid leader sequence of protein A (Abrahmsen et al., *EMBO J.* 4:3901, 1985). Standard cloning procedures described in Maniatis et al. (*Molecular Cloning: A Laboratory Manual*, Cold Spring Harbor Laboratory Press, Cold Spring Harbor, N.Y., 1989) can be used to construct plasmids that direct the translocation of the various species of AAT into the periplasmic space of *E. coli*.

Host cells can be transfected or transformed with the above-described expression or cloning vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known in the art. These include $CaPO_4$ precipitation and electroporation. Successful transfection is generally recognized when any indication of the operation of this vector occurs within the host cell.

Transformation is the introduction of nucleic acid into a cell so that it is replicable, either as an extrachromosomal element or following chromosomal integration. Standard transfection protocols are available. Various treatments, including calcium-based treatments, are described in Sambrook et al., *Molecular Cloning* (2nd ed.), Cold Spring Harbor Laboratory Press, cold Spring Harbor N.Y. (1989). Infection with *Agrobacterium tumefaciens* is used for transformation of certain plant cells, as described by Shaw et al. (*Gene* 23:315, 1983) and WO 89/05859. For mammalian cells, which do not have such cell walls, the calcium phosphate precipitation method described, for example, by Sambrook et al., supra, is preferred. General aspects of mammalian cell host system transformations have been described by Axel in U.S. Pat. No. 4,399,216. Transformations into yeast are typically carried out according to the method of Van Solingen et al. (*J. Bact.* 130:946, 1977) and Hsiao et al. (*Proc. Natl. Acad. Sci. USA* 76:3829, 1979). Other methods for introducing DNA into cells such as by nuclear injection, electroporation, or by protoplast fusion may also be used.

Prokaryotic host cells used to produce a polypeptide of interest (e.g., an AAT) can be cultured as described generally in Sambrook et al., supra.

The mammalian host cells used to produce a polypeptide of interest (e.g., an AAT) can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham and Wallace (*Meth. Enz.* 58:44, 1979), Barnes and Sato *Anal. Biochem.* 102:255, 1980), U.S. Pat. Nos. 4,767,704; 4,657,866; 4,927,762; or 4,560,655; WO 90/03430; WO 87/00195; U.S. Pat. Re. No. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to one of ordinary skill in the art.

The host cells referred to in this disclosure encompass cells in culture as well as cells that are within a host plant or animal.

In an intracellular expression system or periplasmic space secretion system, the recombinantly expressed AAT can be recovered from the cultured cells by disrupting the host cell membrane and/or cell wall (e.g., by osmotic shock or solubilizing the host cell membrane in detergent). Alternatively, in an extracellular secretion system, the recombinant protein can be recovered from the culture medium. As a first step, the culture medium or lysate is centrifuged to remove any particulate cell debris. The membrane and soluble protein fractions are then separated. Crude extracts can be further purified by suitable procedures such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins and ligand affinity using interferon receptor immobilized on a matrix.

An agent that promotes the activity of AAT may do so by increasing the secretion of AAT from a cell. 4-phenylbutyric acid (PBA) has been shown to elicit a marked increase in secretion of 1-AZT, a misfolded but functionally active mutant of α1-antitrypsin, in a model cell culture system (Burrows et al., *Proc. Natl. Acad. Sci. USA* 97:1796-1801, 2000).

As PBA has been used safely in humans, it is an excellent candidate for inclusion in the present compositions and methods, and can be used regardless of the form of AAT.

We may refer to AAT (e.g., Aralast™), therapeutically active variants of AAT (including variants that differ from a wild type AAT by virtue of the manner in which they are post-translationally modified), nucleic acids encoding such polypeptides (i.e., encoding AAT or a therapeutically active variant thereof (e.g., a biologically active fragment or other mutant)), or an agent that increases the activity (e.g., the secretion) of AAT as AAT-related agents. While these agents can be used to treat the patients described herein, any of these AAT-related agents, or any combination thereof, can be combined with at least one additional pharmaceutical agent and/or co-administered to a patient described herein. Where two agents are co-administered, we may refer to "first" and "second" agents; wherein three agents are co-administered, we may refer to "first", "second", and "third" agents; and so forth.

The co-administration can be achieved by combining the agents in a single formulation, in which case the agents would be administered at the same time and by the same route. Formulations containing at least two of the agents described herein (e.g., a first agent such as Aralast™ and a second agent such as an anti-TNFα antibody) are described further below and are within the scope of the present invention. Co-administration can also be achieved when the agents are formulated differently (e.g., one in an intravenous formulation and one in an oral preparation) and administered at the same or different times (e.g., sequentially and within a time frame sufficient to treat the patient). Co-administration of more than one agent or more than one type of agent (e.g., an AAT-related agent and an anti-inflammatory agent) may bring about normoglycemia sooner or produce a normoglycemic state that persists longer after cessation of treatment than with either agent alone (no particular benefit is required as a feature of the invention, however).

Combinations of agents useful in the present methods include the combination of an AAT-related agent and an anti-inflammatory agent. For example, AAT or any other AAT-related agent described herein can be co-administered with an anti-inflammatory agent such as a non-steroidal anti-inflammatory agent (or NSAID). Useful NSAIDs include pyrazolones (e.g., phenylbutazone (Butazolidin™)), anthranilic acids (e.g., mefenamic acid (Ponstel™) and meclofenamate sodium (Meclomen™)), diflunisal (Dolobid™), and acetic acid derivatives (e.g., diclofenac sodium (Voltaren™), indomethacin (Indocin™), sulindac (Clinoril™), etodolac (Lodine™), ketorolac (Toradol™), nabumetone (Relafen™), and tolmetin sodium (Tolectin™)), and propionic acid derivatives (e.g., ibuprofen (Motrin™), fenoprofen (Nalfon™), flurbiprofen (Ansaid™), carprofen (Rimadyl™), ketoprofen (Orudis™), and naproxen sodium (Anaprox™, Naprosyn™), and oxicams (e.g., piroxicam (Feldene™)).

An AAT-related agent can also be co-administered with an antagonist of TNFα. TNFα, also known as cachectin, was so-named because of its ability to cause tumor necrosis in vivo when injected into tumor-bearing mice. TNFα is initially expressed as a 26 kDa membrane-bound protein, and it is subsequently cleaved by TNFα converting enzyme (TACE) to release a soluble 17 kDa monomer that forms homotrimers in the circulation. Recombinant TNFα exists as homodimers, homotrimers, and homopentamers. Functionally, TNFα is believed to have not only antitumor activity, but also to influence immune modulation, inflammation, anorexia, cachexia, septic shock, viral replication, and ematopoiesis.

Useful TNFα antagonists include agents that interfere with TNFα directly (e.g., an anti-TNFα antibody or a soluble TNFα binding agent) or indirectly (e.g., by inhibiting a moiety in the pathway that is required for TNFα to affect cellular processes).

An anti-TNFα antibody is one that selectively binds to TNFα and can be a whole antibody, including a whole human antibody, or an antibody fragment or subfragment thereof. The antibody can be a whole immunoglobulin of any class (e.g., IgG, IgM, IgA, IgD, and IgE), a chimeric antibody, a humanized antibody, or a hybrid antibody with dual or multiple antigen or epitope specificities. The fragments can be, for example, $F(ab)_2$, Fab', Fab, and the like, including hybrid fragments. In addition to classic monovalent antibody fragments such as Fab and scFv, engineered variants such as diabodies, triabodies, minibodies and single-domain antibodies can also be used. The antibody can further be any immunoglobulin or any natural, synthetic or genetically engineered protein that acts like an antibody by binding to TNFα to form a complex. In particular, Fab molecules can be expressed and assembled in a genetically transformed host like E. coli. A lambda vector system is available to express a population of Fab's with a potential diversity equal to or exceeding that of subject generating the predecessor antibody (see Huse et al., Science 246:1275-1281, 1989). The anti-TNFα antibody can be a monoclonal antibody.

As noted, adalimumab (HUMIRA®) and/or infliximab (REMICADE®) can be used in the present compositions and methods. CDP571 (a humanized monoclonal anti-TNFα antibody), other monoclonal anti-TNFα antibodies, and D2E7 (a human anti-TNF mAb) can also be used.

Methods of making and using antibodies are now well-known in the art (see, e.g., Antibodies, Ed Harlow and David Lane (Eds.), CSHL Press, Cold Spring Harbor, N.Y., 1988; Using Antibodies, Ed Harlow and David Lane (Eds.), CSHL Press, Cold Spring Harbor, N.Y., 1998), and those techniques can be applied to generate an anti-TNFα antibody useful in the present methods.

Alternatively, or in addition, an AAT-related agent can be formulated with and/or co-administered with an agent that selectively inhibits a moiety with the TNFα signaling pathway (e.g., a soluble receptor antagonist). The receptor can be joined to an immunoglobulin molecule or a portion thereof (e.g., an Fc region (e.g., an Fc region of an IgG molecule)). More specifically, the soluble receptor antagonist can be etanercept (Enbrel™). Etanercept is a recombinant fusion protein consisting of two soluble TNF receptors joined by the Fc fragment of a human IgG1 molecule. Etanercept is currently approved only for rheumatoid arthritis and is provided as a subcutaneous injection of 25 mg given twice a week. This regimen produces peak blood levels in an average of 72 hours.

The soluble receptor antagonist can include a full-length, soluble TNFα receptor or a portion or other mutant thereof that retains sufficient TNFα binding activity to reduce TNFα activity to a clinically useful extent. For example, the antagonist can be, or can include, the previously identified C-terminal truncated form of the soluble human TNF receptor type I (sTNF-RI) that was included in the antagonist referred to as PEG-sTNF-RI or PEG(sTNF-RI) (p55). This antagonist has been produced in E. coli, which is a commonly used source of recombinant proteins, and it contains the first 2.6 of the four domains of the intact sTNF-RI molecule. As noted, the receptor can be PEGylated. A monoPEGylated form of this molecule has been produced using a 30 kDa methoxyPEG aldehyde with approximately 85% selectivity for the N-terminal amino group. Antagonists that contain less than a full-length TNFα receptor may be less immunogenic than those containing a full-length receptor. The sites of PEGylation and the molecular weight of the PEG used can vary and can be identical to those of PEG-sTNF-RI. The 30 kDa PEG used previously may confer a longer serum half-life to antagonists than lower molecular weight PEGs. (see Edwards et al., Adv. Drug. Delivery Res. 55:1315-1336, 2003).

Other useful TNFα inhibitors, any of which, or any combination of which, can be administered in connection with AAT, include agents that selectively inhibit TNFα expression, such as RNA molecules that mediate RNAi (e.g., a TNFα selective siRNA or shRNA) and antisense oligonucleotides. More specifically, one can administer a molecule that mediates RNAi (e.g., a short interfering nucleic acid (siNA), a short interfering RNA (siRNA), a double-stranded RNA (dsRNA), or a short hairpin RNA (shRNA) as described in published U.S. Patent Application No. 20050227935, the contents of which are incorporated herein by reference in their entirety. Accordingly, alternatively, or in addition, an AAT-related agent can be formulated with and/or co-administered with an agent that selectively inhibits TNFα expression (e.g., an anti-TNFα RNA molecule that mediates RNAi).

Alternatively, or in addition, patients can be treated with an AAT-related agent and, as an agent that selectively inhibits a moiety within the TNFα signaling pathway, an inhibitor of TACE (TNFα converting enzyme). Compositions containing an AAT-related agent and an inhibitor of TACE are, as are the other combinations of agents described herein, within the scope of the invention.

Alternatively, or in addition, an AAT-related agent can be formulated with and/or co-administered with a small organic or inorganic compound that inhibits TNFα (e.g., LMP420; Haraguchi et al., AIDS Res. Ther. 3:8, 2006), thalidomide or a thalidomide analog, or a phosphodiesterase type IV inhibitor. Thalidomide is described in U.S. Pat. No. 2,830,991, the content of which is hereby incorporated by reference in its entirety. This agent has the chemical name 3-phthalimidopiperidine dione 2,6, and it is a derivative of glutamic acid. Useful compositions, including those formulated for topical administration, can include thalidomide, or an analog thereof, solubilized in polyethylene glycol. Suitable preparations include those described in U.S. Pat. No. 5,443,824, the content of which is hereby incorporated by reference in its entirety. Thalidomide has been suggested for oral administration at dosage levels in the range of 10 mg to 300 mg.

Suitable phosphodiesterase type IV inhibitors include rolipram (e.g., (–)-rolipram). Other suitable phosphodiesterase type IV inhibitors include: (1) 1,3-Dibutyl-3,7-dihydro-7-(2-oxopropyl)-1H-purine-2,6-dione (Denbufyllines, BRL 30892); (2) 4-[(3-butoxy-4-methoxyphenyl)methyl]-2-imidazolidinone (Ro 20-1724); (3) 4-[3-(cyclopentyloxy)-4-methoxyphenyl]-2-pyrrolidinone (rolipram, ZK 62711); (4) 5,6-diethoxybenzo[b]thiophene-2-carboxylic acid (Tibenelast, LY 186655); (5) 3-ethyl-1-(3-nitrophenyl)-2,4 (1H,3H)-quinazolinedione (nitraquazones, TVX 2706); (6) 6-(3,6-dihydro-6-methyl-2-oxo-2H-1,3,4-thiadiazin-5-yl)-1-(3,4-dimethoxybenzoyl)-1,2,3,4-tetrahydro-4,4-dimethylquinoline (EMD 54622); (7) 1-ethyl-4-[(1-methylethylidene)hydrazino]-1H-pyrazolo[3,4-b]pyridine-5-carboxylic acid ethyl ester (etazolates); (8) N-hydroxy-5,6-dimethoxy-benzo[b]thiophene-2-carboximidamide (Org 30029); (9) 2-amino-6-methyl-4-propyl-(1,2,4)triazolo[1,5-a]pyrimidin-5(4H)-one (ICI-63197); and (10) 6-[4-(difluoromethoxy)-3-methoxyphenyl]-3(21-1)-pyridazinone (zardaverines) (as well as their pharmacologically compatible salts).

Phosphodiesterase type IV inhibitors, particularly racemic or optically active rolipram, can be produced as described in U.S. Pat. No. 4,193,626 or according to WO 92/06077, the contents of which is hereby incorporated by reference in their entirety. The daily total dose of rolipram is usually 0.001-10 mg (e.g., 0.01-5 mg). If (−) rolipram is administered as the active ingredient, the daily dose is preferably 0.001-5 mg. After several days of titration, the total dose can be increased significantly if necessary. Additional guidance can be obtained from known literature, including U.S. Pat. No. 5,891,904, the content of which is hereby incorporated by reference in its entirety.

Alternatively, or in addition, an AAT-related agent can be formulated with and/or co-administered with an antagonist of an inflammatory cytokine (e.g., an antagonist of IL-1, IL-6, or IL-8). A known and useful IL-1 antagonist, which may be incorporated in the present compositions and methods is anakinra (KINERET™).

Alternatively, or in addition, an AAT-related agent can be formulated with and/or co-administered with an agonist of a glucagon-like peptide (GLP) receptor or an agonist of an exendin receptor (e.g., GLP-1, Exendin-3, Exendin-4 or GLP-1(7-36)-amide). Exendin-4, which is also known as exenatide (BYETTA®) is within a relatively new class of medications approved for the treatment of Type 2 diabetes. It is an incretin mimetic, which has glucoregulatory effects (the known incretins, GLP-1 and GIP, are not useful in treatment because their circulating half-life is too short; exenatide was found to have a similar amino acid sequence, triggers similar responses, and has a relatively long half-life)). It is to be used in conjunction with oral medications such as metformin and/or a sulfonylurea to improve glucose control. According to current protocols, the medication is injected twice per day, and the typical human response is both an improvement in the release of internal insulin by the pancreas and suppression of pancreas glucagon release.

Alternatively, or in addition, an AAT-related agent can be formulated with and/or co-administered with an agonist of CD3 (e.g., an anti-CD3 antibody).

As noted above, as many of the agents, or types of agents, useful in the present methods are known to be useful in treating other conditions, one of ordinary skill in the art has access to substantial information that can be used in formulating and administering the present agents or combinations of agents for the purposes described herein. Should one wish to conduct toxicity studies, that may be done.

Toxicity and therapeutic efficacy of any given agent can be determined by standard pharmaceutical procedures in cell cultures or experimental animals. For example, cell cultures and experimental animal models can be used for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects. This is particularly true if chronic administration is contemplated.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the 1050 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

A therapeutically effective amount of a polypeptide (i.e., an effective dosage) (e.g., of an AAT, an antibody, or soluble receptor antagonist) can range from about 0.001 to 30 mg/kg body weight (e.g., from about 0.01 to 25 mg/kg body weight; from about 0.1 to 20 mg/kg body weight; or from about 1 to 10 mg/kg (e.g., 2 to 9 mg/kg, 3 to 8 mg/kg, 4 to 7 mg/kg, or 5 to 6 mg/kg body weight)). The polypeptide can be administered on an acute or chronic basis. For example, a polypeptide can be administered one time per week for between about 1 to 10 weeks (e.g., 2 to 8 weeks, 3 to 7 weeks, or for about 4, 5, or 6 weeks). Despite this guidance and other dosing and formulation guidance provided here, one of ordinary skill in the art will appreciate that certain factors will influence the dosage and timing required to effectively treat a subject. These factors include, but are not limited to, the severity of the disease or disorder, previous treatments, the general health and/or age of the subject, and other diseases present. Moreover, treatment of a subject with a therapeutically effective amount of a polypeptide (e.g., an antibody) can include a single treatment or, preferably, can include a series of treatments.

For antibodies, dosages of 0.1 mg/kg of body weight (generally 10 mg/kg to 20 mg/kg) may prove most effective. Generally, partially human antibodies and fully human antibodies have a longer half-life within the human body than other antibodies. Accordingly, lower dosages and less frequent administration is often possible when these types of antibodies are used. The treatment regime may also vary depending upon whether modifications such as lipidation have been used to stabilize the antibodies and/or to enhance uptake and tissue penetration. A method for lipidation of antibodies is described by Cruikshank et al. (*J. Acquired Immune Deficiency Syndromes and Human Retrovirology* 14:193, 1997)).

In the present case, one of ordinary skill in the art can consider the dosages of an AAT (e.g., of ARALAST™, PROLASTIN™, or ZEMAIRA™) previously administered in order to determine a safe and effective dose for the indications described here. The recommended dosage of ARALAST™ is 60 mg/kg body weight (e.g., 15-90 mg/kg), and it is typically administered once weekly by intravenous infusion. In accordance with previous recommendations, ARALAST™ should be administered within three hours after it has been reconstituted to avoid the potential ill effect of any inadvertent microbial contamination that may have occurred (e.g., during reconstitution). As with other, similarly administered therapeutics, any unused contents should be discarded. With respect to infusion, ARALAST™ can be administered at a rate that does not exceed 0.08 ml/kg body weight/minute (2.0 mg/kg body weight/minute). If adverse events occur, the rate should be reduced or the infusion interrupted until the symptoms subside. The infusion may then be resumed at a rate that is better tolerated by the subject. Over time, the treatment can be discontinued if and when the patient's diabetic or pre-diabetic symptoms are sufficiently well resolved. Other parenteral routes of administration include inhalation. For example, an AAT can be incorporated into a metered-dose aerosol unit containing, for example, a microcrystalline suspension of the drug in a mixture of halogenated hydrocarbon propellants alone or with a carrier such as oleic acid.

The current methods can be carried out using any of the following routes of administration: subcutaneous, intravenous, intrathecal, intramuscular, intranasal, oral, transepidermal, parenteral, by inhalation, or intracerebroventricular. Intracerebroventricular and intrathecal routes are more invasive and are expected to only be used with severe disorders, The patients described herein can be subjected to an acute regimen, in which case they may be given just a single dose of one or more of the agents described, 2-3 doses of one or more of the agents described, or up to a one-month treatment (of daily or repeated administrations). While our experimental results indicate that acute treatment may be effective and sufficient, an acute regimen may need to be repeated, or the treatment may be chronic (e.g., ongoing for more than about one month (e.g., for 30 days or more)).

Generally, and by way of illustration, TNFα antagonists may be administered subcutaneously and may be administered by that route at a dosage in the range of 5 mg to 50 mg (for acute or chronic regimens); intranasally and may be administered by that route at a dosage in the range of 0.1 mg to 10 mg (for acute or chronic regimens); intramuscularly and may be administered by that route at a dosage in the range of 25 mg to 100 mg; intravenously and may be administered by that route at a dosage in the range of 2.5 mg/kg to 20 mg/kg; intrathecally and may be administered by that route at a dosage in the range of 0.1 mg to 25 mg (e.g., administered from once a day to every three months); transepidermally and may be administered by that route at a dosage in the range of 10 mg to 100 mg; by inhalation and may be administered by that route at a dosage in the range of 0.2 mg to 40 mg; intracerebroventricularly and may be administered by that route at a dosage in the range of 0.1 mg to 25 mg (e.g., administered once a day to once every 3 months); orally and may be administered by that route at a dosage in the range of 10 mg to 300 mg.

Generally, and by way of illustration, etanercept may be administered intramuscularly and may be administered by that route at a dosage in the range of 25 mg to 100 mg; subcutaneously and may be administered by that route at a dosage in the range of 5 mg to 50 mg; intrathecally and may be administered by that route at a dosage in the range of 0.1 mg to 25 mg (e.g., administered from once a day to once a month).

Generally, and by way of illustration, infliximab may be administered intravenously and may be administered by that route at a dosage in the range of 2.5 mg/kg to 20 mg/kg; intrathecally and may be administered by that route at a dosage in the range of 0.1 mg/kg to 5 mg/kg (e.g., administered from once a week to once every three months).

Of the available routes of administration, we expect etanercept and infliximab will be administered either subcutaneously, intramuscularly, intraventricularly, or intrathecally, or intravenously.

Any of the methods described herein can be carried out in conjunction with first-line therapies designed to reduce the major risk factors for diabetes and cardiovascular disease. These include programs and pharmacological intervention to reduce or stop smoking and to reduce LDL cholesterol, blood pressure, weight, and glucose levels to the recommended levels. Excess weight also contributes to insulin resistance because too much fat interferes with muscles' ability to use insulin. Lack of exercise further reduces muscles' ability to use insulin.

EXAMPLES

Animals:

Female NOD (NOD/LtJ) mice and NOD.SCID (NOD.CB17-Prkdc$^{scid}$/J) were purchased from Jackson Laboratories (Bar Harbor, Me.) at 4 weeks of age and maintained under pathogen-free conditions in a conventional animal facility at Massachusetts General Hospital (Boston, Mass.). All animal studies were approved by our institutional review boards. The blood glucose levels of NOD mice were monitored weekly with the ACCU-CHECK® blood glucose monitor system (Roche, Indianapolis, Ind.). When non-fasting blood glucose levels of NOD mice were found to be >300 mg/dl on three consecutive days, the NOD mice were diagnosed as new onset diabetic mice, and treatment commenced. For syngeneic islet transplant recipients, blood glucose levels were checked at the time of transplantation, then daily for the first two weeks, and then 2 to 3 times per week afterward.

Islet Isolation:

NOD.SCID mice at 10-12 weeks of age were used as donors for islet transplants. Islets were isolated using a standard method, which was a modification of the method of Gotoh et al. in which the pancreatic duct is distended with collagenase P (Gotoh et al., *Transplantation* 40:437, 1985). After purification on a Histopaque gradient (Histopaque®-1077, Sigma Chemical Co., St. Louis, Mo.), islets with diameters between 75 and 250 μm were hand picked and transplanted under the renal capsule. Each recipient received 600-800 NOD.SCID islets.

Reagents and Treatment Protocols:

ARALAST™:

ARALAST™ (α1-proteinase inhibitor, human) is a major serum serine-protease inhibitor that inhibits the enzymatic activity of neutrophil elastase, cathespin G, proteinase 3, thrombin, trypsin, and chymotrypsin. ARALAST™ was purchased from Baxter (Westlake Village, Calif.) and was given at a dose of 2 mg i.p. every 3 days, for a total of 5 injections.

Monoclonal Anti-Tumor Necrosis Factor-α:

Antibody produced in hamster clone TN3-19.12 (hamster IgG1) mAb specific for murine TNF, was purchased from Sigma (St. Louis, Mo.) and was given at a dose of 100 mg i.p. every other day for 10 doses.

Exendin-4:

Exendin-4, an agonist of the glucagon-like peptide (GLP-1) receptor, was purchased from Sigma (Saint Louis, Mo.) and was administered i.p. once a day for four sets of five consecutive days, with a two-day break between the four treatment administrations.

In Vivo Insulin Signaling Studies:

In vivo insulin signaling experiments were performed on mice after a 16 hour fast. Mice were injected i.p. with 20 U/kg BW of human insulin (Eli Lilly) or saline. Skeletal muscle (gastronemius) was dissected and frozen in liquid nitrogen for immunoblotting analysis of insulin signaling proteins.

Immunoblotting (IB):

Skeletal muscle (gastronemius), obtained in the context of our in vivo insulin signaling studies, was homogenized in a modified radioimmunoprecipitation assay (RIPA) buffer containing 50 mM Tris-HCl, 1 mM EDTA, 1% NP-40, 0.25% sodium deoxycholate, 150 mM NaCl, 1 mM PMSF, 200 μM Na$_3$VO$_3$, supplemented with 1% protease inhibitor cocktail (Sigma), and 1% tyrosine phosphatase inhibitor cocktail (Sigma). Cell homogenates were incubated on ice for 45 minutes to solubilize all proteins, and insoluble portions were removed by centrifugation at 14,000 g at 4° C. for 15 minutes. Whole cell lysates were separated by SDS-polyacrylamide gel electrophoresis (PAGE). Proteins on the gels were transferred to Hybond ECL nitrocellulose membrane (Amersham Pharmacia Biotech, Piscataway, N.J.). The transferred membranes were blocked, washed, incubated with various primary antibodies, and followed by incubation with horseradish peroxidase-conjugated secondary antibodies. Rabbit polyclonal anti-insulin receptor (IR; pY1162/1163) and anti-insulin receptor substrate-1 (IRS-1; pY612) antibodies were purchased from BioSource (BioSource International, Inc., Camarillo, Calif.). Rabbit polyclonal anti-IR antibody was purchased from Santa Cruz Biotech (Santa Cruz, Calif.). Rabbit polyclonal anti-IRS-1 was obtained from Upstate (Lake Placid, N.Y.). Visualization was done with chemiluminescence reagent, using the ECL Western Blotting Analysis System (Amersham Pharmacia Biotech). The blots were quantified using densitometry (Molecular Dynamics, Sunnvale, Calif.).

Insulin Tolerance Test:

Insulin tolerance test (ITT) was performed on (1) new onset diabetic NOD mice treated with ARALAST™; (2) new onset diabetic NOD mice treated with anti-TNF-α mAb; (3) new onset diabetic NOD mice treated with ARALAST™ and anti-TNF-α mAb; (4) age matched non-diabetic NOD mice (NOD); and (5) new onset diabetic NOD mice (NODsp). Food was withheld 3 hours before testing. Animals were weighed and blood samples were collected at 0 minutes. The animals were then injected i.p. with 0.75 U/kg of regular human insulin (Novolin, Novo Nordisk Pharmaceutical Industries, Inc. Clayton, N.C.), and blood samples were collected 15, 30 and 60 minutes later. The results were expressed as percentage of initial blood glucose concentration Results:

The results we obtained by treating animals with ARALAST™, anti-TNF-α antibodies, Exendrin-4, and various combinations of these agents are shown in Table 1. In all paradigms, normoglycemia was achieved, often after a brief period of time, in 80-90% of mice treated with either ARALAST™, anti-TNF-α antibodies and 65% in the animals treated with Exendrin-4 alone. Two animals were outliers, achieving normoglycemia only after 49 and 55 days (see column 2 of Table 1). The last column shows how long the animals have been normoglycemic. The animals were still alive as of this writing.

TABLE 1

Summary of different treatment groups using Aralast, Anti-TNF-α, or Exendin-4.

| Treatment | Normoglycemia achieved (range in days) | Normoglycemic/ Total number of mice treated | Days after treatment |
|---|---|---|---|
| Aralast ™ | 1-22 (49, 55) | 14/16 | 90-300 |
| Anti-TNF-α | 1-38 | 22/24 | 180-230 |
| Aralast ™ + Anti-TNF-α | 1-12 | 11/14 | 120-250 |
| Aralast ™ + Exendin-4 | 1, 1, 4, 15, 38 | 5/5 | 180-250 |
| Anti-TNF-α + Exendin-4 | 1, 1, 2, 11, 22 | 5/5 | 170-210 |
| Exendin-4 | 1, 14, 41, 55 | 4/6 | 170-300 |

Viral Mediated Gene Delivery of AAT:

A murine AAT cDNA sequence was delivered to mouse liver by i.p. or i.v. injection using an AAV8 (Adeno-Associated Virus 8) vector in which transcription was restricted to hepatocytes by a Major Urinary Protein transcriptional element. Production of AAT commenced within several days. In one variation, the natural leader sequence of the mouse AAT was substituted with one derived from an Ig-kappa chain, and an HA epitope tag was added to further distinguish it from endogenous mouse AAT.

We tested the efficacy of AAT in a passive transfer model of Type 1 diabetes (T1D). In this model, transfer of splenic mononuclear leukocytes, i.e., immunocompetent T cells, from diabetic mice into NOD.SCID mice, which do not spontaneously develop diabetes, results in the rapid onset of T1D.

On day 0, NOD.SCID mice were infused with $5 \times 10^7$ splenic cells from spontaneously diabetic NOD (NODsp) mice. Mice in group A were injected with phosphate-buffered saline (PBS); mice in groups B and C were injected with AAV constructs that encoded murine AAT as described above; mice in group D were injected with AAV vector that lacked an insert ("empty vector"). All injections were in 250 uL volumes.

Glycemia was monitored on a daily basis thereafter, until day 65, when the mice were sacrificed. As shown in Table 2, the onset of hyperglycemia (blood glucose levels of greater than 250 mg/dL) was delayed in the groups receiving AAV-AAT (groups C and D) as compared to the PBS injected control animals (group A). As of this writing the empty vector control group, group D, was under study.

Serum was collected for analysis of AAT levels. Liver, muscle, fat, pancreas, PLN were collected for PCR analysis of AAT expression.

TABLE 2

Effect of AAV-mediated gene delivery of AAT on blood glucose levels in a diabetic mouse model

| Groups | Donor cells | Recipient | Treatment | Day of hyperglycemia (BG > 250 mg/dL) |
|---|---|---|---|---|
| A | NODsp | NOD.SCID (n = 5) | PBS | 9, 10, 11, 13, 15 |
| B | NODsp | NOD.SCID (n = 5) | M4-AAT AAV8 | 36, 36, 40, 40, >65 |
| C | NODsp | NOD.SCID (n = 5) | M4-AATpDISplay AAV8 | 28, 28, 30, 33, 33 |
| D | NODsp | NOD.SCID (n = 5) | AAV8 ("empty vector") | >8*, >8*, >8*, >8*, >8* |

*Group D was a new group and the mice were only at day 8 after receiving spleen cells. Two of 5 mice had blood glucose levels >200 mg/dL on day 8.

What is claimed is:

1. A method of treating a patient who has been diagnosed as having Type 2 diabetes, the method consisting essentially of:
   (a) identifying a patient who has been diagnosed as having Type 2 diabetes; and
   (b) administering to the patient a therapeutically effective amount of an α1-antitrypsin polypeptide or a nucleic acid molecule that encodes the α1-antitrypsin polypeptide, wherein the α1-antitrypsin polypeptide has at least 95% identity to a sequence of a wild type α1-antitrypsin polypeptide.

2. The method of claim 1, wherein the patient is a human patient.

3. The method of claim 2, wherein the human patient is a child or adolescent.

4. The method of claim 1, wherein the patient has been diagnosed as having Type 2 diabetes on the basis of one or more of the following findings:
   (a) hyperglycemia in conjunction with a normal or elevated level of insulin;
   (b) hyperglycemia in conjunction with evidence of pancreatic β cell maintenance;

(c) hyperglycemia in conjunction with a blunted blood glucose response to insulin; and (d) hyperglycemia and a family history of Type 2 diabetes.

5. The method of claim 4, wherein the normal or elevated level of insulin is reflected by a normal or elevated level of C-peptide.

6. The method of claim 4, wherein the patient is a human patient.

7. The method of claim 6, wherein the human patient is an adult.

8. A method of treating a patient who has been diagnosed as being at greater than average risk for developing Type 2 diabetes, the method comprising:
(a) identifying a patient who has been diagnosed as being at greater than average risk for developing Type 2 diabetes; and
(b) administering to the patient a therapeutically effective amount of an α1-antitrypsin polypeptide or a nucleic acid molecule that encodes the α1-antitrypsin polypeptide, wherein the α1-antitrypsin polypeptide has at least 95% identity to a sequence of a wild type α1-antitrypsin polypeptide.

9. The method of claim 8, wherein the patient has been diagnosed as being at risk for developing Type 2 diabetes on the basis of one or more of the following findings:
(a) impaired glucose tolerance with or without features of metabolic syndrome;
(b) normal or impaired glucose tolerance with hyperinsulinemia; and
(c) impaired glucose tolerance and a family history of Type 2 diabetes.

10. The method of claim 9, wherein the features of metabolic syndrome include abdominal obesity, atherogenic dyslipidemia, a prothrombotic state, elevated blood pressure, or elevated levels of inflammatory cytokines.

11. The method of claim 9, wherein the hyperinsulinemia is reflected by an elevated level of C-peptide.

12. The method of claim 9, wherein the patient who has been diagnosed as being at risk for developing Type 2 diabetes is a female patient who has had gestational diabetes.

13. The method of claim 8, wherein the patient is a human patient.

14. The method of claim 13, wherein the human patient is an adult.

15. A method of treating a patient who has been diagnosed as having Type 2 diabetes, the method consisting of:
(a) identifying a patient who has been diagnosed as having Type 2 diabetes; and
(b) administering to the patient a therapeutically effective amount of an α1-antitrypsin polypeptide or a nucleic acid molecule that encodes the α1-antitrypsin polypeptide, wherein the α1-antitrypsin polypeptide has at least 95% identity to a sequence of a wild type α1-antitrypsin polypeptide.

16. The method of claim 15, wherein the patient is a human patient.

17. The method of claim 16, wherein the human patient is a child or adolescent.

18. The method of claim 15, wherein the patient has been diagnosed as having Type 2 diabetes on the basis of one or more of the following findings:
(a) hyperglycemia in conjunction with a normal or elevated level of insulin;
(b) hyperglycemia in conjunction with evidence of pancreatic 0 cell maintenance;
(c) hyperglycemia in conjunction with a blunted blood glucose response to insulin; and
(d) hyperglycemia and a family history of Type 2 diabetes.

19. The method of claim 18, wherein the normal or elevated level of insulin is reflected by a normal or elevated level of C-peptide.

20. The method of claim 18, wherein the patient is a human patient.

21. The method of claim 20, wherein the human patient is an adult.

22. The method of claim 1, wherein the patient is administered a therapeutically effective amount of an α1-antitrypsin polypeptide that has at least 99% identity to a sequence of a wild type α1-antitrypsin polypeptide.

23. The method of claim 1, wherein the α1-antitrypsin polypeptide is joined to a portion of an immunoglobulin or an albumin.

24. The method of claim 23, wherein the portion of the immunoglobulin is an Fc region of an IgG molecule.

25. The method of claim 8, wherein the patient is administered a therapeutically effective amount of an α1-antitrypsin polypeptide that has at least 99% identity to a sequence of a wild type α1-antitrypsin polypeptide.

26. The method of claim 8, wherein the α1-antitrypsin polypeptide is joined to a portion of an immunoglobulin or an albumin.

27. The method of claim 26, wherein the portion of the immunoglobulin is an Fc region of an IgG molecule.

28. The method of claim 15, wherein the patient is administered a therapeutically effective amount of an α1-antitrypsin polypeptide that has at least 99% identity to a sequence of a wild type α1-antitrypsin polypeptide.

29. The method of claim 15, wherein the α1-antitrypsin polypeptide is joined to a portion of an immunoglobulin or an albumin.

30. The method of claim 15, wherein the portion of the immunoglobulin is an Fc region of an IgG molecule.

31. The method of any of claims 1, 8, and 15, wherein the α1-antitrypsin polypeptide is a full-length α1-antitrypsin polypeptide.

32. The method of claim 31, wherein the full-length α1-antitrypsin polypeptide is a human α1-antitrypsin polypeptide.

33. The method of claim 8, wherein the method further comprises administering an agent that selectively inhibits TNFα or a moiety within the TNFα signaling pathway.

34. The method of claim 33, wherein the agent that inhibits TNFα is an anti-TNFα antibody.

35. The method of claim 34, wherein the anti-TNFα antibody is a human, humanized, chimeric or single chain antibody.

36. The method of claim 34, wherein the anti-TNFα antibody is a monoclonal antibody.

37. The method of claim 34, wherein the anti-TNFα antibody is adalimumab or infliximab.

38. The method of claim 33, wherein the agent that selectively inhibits a moiety within the TNFα signaling pathway is a soluble receptor antagonist.

39. The method of claim 38, wherein the soluble receptor antagonist comprises an immunoglobulin-like molecule.

40. The method of claim 38, wherein the soluble receptor antagonist is etanercept.

41. The method of claim 38, wherein the soluble receptor antagonist comprises polyethylene glycol.

42. The method of claim 41, wherein the soluble receptor antagonist is PEG-sTNF-RI (p55).

43. The method of claim 33, wherein the agent that selectively inhibits TNFα is an RNA molecule that mediates RNAi.

44. The method of claim 43, wherein the RNA molecule that mediates RNAi is an siRNA or an shRNA.

45. The method of claim 33, wherein the agent that selectively inhibits TNFα is a small organic or inorganic compound.

46. The method of claim 45, wherein the small organic or inorganic compound is LMP420.

47. The method of claim 8, wherein the method further comprises administering an antagonist of an inflammatory cytokine.

48. The method of claim 47, wherein the inflammatory cytokine is IL-1 or IL-6.

49. The method of claim 48, wherein the inflammatory cytokine is IL-1.

50. The method of claim 49, wherein the antagonist is anakinra.

51. The method of claim 8, wherein the method further comprises administering an agonist of a glucagon-like peptide (GLP) receptor or an agonist of an exendin receptor.

52. The method of claim 51, wherein the GLP receptor is GLP-1.

53. The method of claim 51, wherein the agonist of the GLP receptor or the agonist of the exendin receptor is exendin-3, exendin-4, or GLP-1(7-36)-amide.

54. The method of claim 8, wherein the method further comprises administering a CD3 antagonist.

55. The method of claim 54, wherein the CD3 antagonist is an anti-CD3 antibody.

* * * * *

UNITED STATES PATENT AND TRADEMARK OFFICE
CERTIFICATE OF CORRECTION

PATENT NO. : 8,623,830 B2  Page 1 of 1
APPLICATION NO. : 12/441064
DATED : January 7, 2014
INVENTOR(S) : Jeffrey Flier, Maria Koulmanda and Terry B. Strom It is certified that error appears in the above-identified patent and that said Letters Patent is hereby corrected as shown below:

On the Title Page

Item (56) (Other Publications), Line 21, delete "Didabetes" and insert -- Diabetes --.

Item (56) (Other Publications), Line 37, delete "Lewis at al,," and insert -- Lewis et al., --.

Item (56) (Other Publications), Line 37, delete "Monotherapv" and insert -- Monotherapy --.

Item (56) (Other Publications), Line 40, delete "Nielsen at al.," and insert -- Nielsen et al. --.

Item (57) (Abstract), Line 4, delete "a1 antitrypsin (AAT)" and insert -- α1-antitrypsin (AAT) --.

Item (57) (Abstract), Line 7, delete "a1-antitrypsin." and insert -- α1-antitrypsin. --.

In the Claims

In Column 31, Line 64, Claim 18, delete "0 cell" and insert -- β cell --.

Signed and Sealed this
Twenty-seventh Day of May, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,623,830 B2
APPLICATION NO. : 12/441064
DATED : January 7, 2014
INVENTOR(S) : Flier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1064 days.

Signed and Sealed this
Nineteenth Day of May, 2015

Michelle K. Lee
*Director of the United States Patent and Trademark Office*